United States Patent
Sun

(10) Patent No.: US 6,257,234 B1
(45) Date of Patent: Jul. 10, 2001

(54) APPARATUS AND METHOD FOR DETERMINING RESPIRATORY MECHANICS OF A PATIENT AND FOR CONTROLLING A VENTILATOR BASED THEREON

(75) Inventor: Jianguo Sun, Belmont, CA (US)

(73) Assignee: Respironics, Inc., Pittsburgh, PA (US)

( * ) Notice: Subject to any disclaimer, the term of this patent is extended or adjusted under 35 U.S.C. 154(b) by 0 days.

(21) Appl. No.: 09/376,211

(22) Filed: Aug. 18, 1999

Related U.S. Application Data

(60) Provisional application No. 60/097,490, filed on Aug. 21, 1998.

(51) Int. Cl.$^7$ .................................................. A61M 16/00
(52) U.S. Cl. ................................ 128/204.18; 128/204.23
(58) Field of Search ..................... 128/204.18, 204.21, 128/204.23; 600/533, 529, 538

(56) References Cited

U.S. PATENT DOCUMENTS

| | | |
|---|---|---|
| 3,834,381 | 9/1974 | Peterson . |
| 4,022,193 | 5/1977 | Franetzki et al. . |
| 4,031,885 | 6/1977 | Davis et al. . |
| 4,051,843 | 10/1977 | Franetzki et al. . |
| 4,122,839 | 10/1978 | Franetzki et al. . |
| 4,259,967 | 4/1981 | Vooren et al. . |
| 4,802,492 | 2/1989 | Grunstein . |
| 5,107,830 | 4/1992 | Younes . |
| 5,233,998 | 8/1993 | Chowienczyk et al. . |
| 5,316,009 | 5/1994 | Yamada . |
| 5,704,345 | 1/1998 | Berthon-Jones . |
| 5,720,709 | 2/1998 | Schnall . |
| 5,735,267 | 4/1998 | Tobia . |
| 5,884,622 | 3/1999 | Younes . |
| 6,068,602 | 5/2000 | Tham et al. . |

FOREIGN PATENT DOCUMENTS

| | | |
|---|---|---|
| 0 521 515 B1 | 10/1996 | (EP) . |

OTHER PUBLICATIONS

Bates et al., "A Comparison of Interrupter and Forced Oscillation Measurements of Respiratory Resistance in the Dog," 1992, American Physiological Society, 46–52.

Bates et al., "Respiratory Resistance with Histamine Challenge by Single–Breath and Forced Oscillation Methods", 1986, American Physiological Society, 873–880.

Bates et al., "A Theoretical Analysis of Interrupter Technique for Measuring Respiratory Mechanics", 1988, American Physiological Society, 2204–2214.

Calhoun et al., "Normal Nasal Airway Resistance in Noses of Different Sizes and Shapes", 1989, Otolaryngology—Head and Neck Surgery, vol. 103, 1990.

Chatburn, "A New System for Understanding Mechnical Ventilators", 1991, Respiratory Care, vol. 36 No. 10, 1123–1155.

(List continued on next page.)

*Primary Examiner*—Glenn K. Dawson
*Assistant Examiner*—Teena Mitchell
(74) *Attorney, Agent, or Firm*—Michael W. Haas

(57) ABSTRACT

A ventilation system is controlled by detecting the resistance and elastance of the patient's respiratory system and adjusting the flow supplied by the ventilator accordingly. In one embodiment, the resistance is detected by controlling the ventilator to superimpose at least one forced single oscillation on the flow and observing the reaction of the respiratory system. In another embodiment, the elastance is detected by controlling the ventilator to supply a pressure which has the effect of temporarily occluding the respiratory system, waiting until the respiratory system has reached equilibrium, and observing the resulting state of the respiratory system. The detection techniques of these two embodiments can be used together.

33 Claims, 10 Drawing Sheets

OTHER PUBLICATIONS

Chiang et al., "Determination of Total Respiratory Resistance in Health and Disease by Added External Resistance", 1986, 1988, Chest, vol. 93, No. 3, 537–540.

Chowienczyk et al., "A Flow Interruption Devise for Measurement of Airway Resistance", 1991, Eur Respir J., vol. 4, 623–628.

Daroczy et al., "Generation of Optimum Pseudorandom Signals for Respiratory Impedance Measurements", 1990, Int J Biomet Comput, vol. 25, 21–31.

Frank et al., "Comparative Sensitivity of Four Methods for Measuring Changes in Respiratory Flow Resistance in Man", 1971, Journal of Applied Physiology, vol. 31, No. 6, 934–937.

Green et al., "Improved Computation of Respiratory Resistance as Measured by Transiently Increased Resistance", 1990, Medical & Biological Engineering &Computing, vol. 28, 50–53.

Gimeno et al., "Variability of Forced Oscillation (Siemens Siregnost FD 5) Measurements of Total Respiratory Resistance in Patients and Healthy Subjects", 1992, Annals of Allergy, vol. 71, 56–60.

Hantos et al., "Forced Oscillatory Impedance of the Respiratory System at Low Frequencies", 1986, The American Physiological Society, 123–132.

Jackson et al., "A Reevaluation of the Interrupter Technique for Airway Resistance Measurement", 1974, Journal of Applied Physiology, vol. 36, No. 2, 264–268.

Lutchen et al., "Optimal Ventilation Waveforms for Estimating Low–Frequency Respiratory Impedance", 1993, The American Physiological Society, 478–488.

Lutchen et al., "Low–Frequency Respiratory Mechanics using Ventilator–Driven Forced Oscillations", 1993, The American Physiological Society, 2549–2560.

Mayewski et al., "Measurement of Static Pressure–Volume Relationships of the Lung and Thorax", Adult Pulmonary Function Testing, 79–113.

Morozoff et al., "Real–Time Display of Flow–Pressure–Volume Loops", 1992, Biomedical Instrumentation and Technology, 312–317.

Neild, et al., "The Repeatability and Validity of Respiratory Resistance Measured by the Forced Oscillation Technique", 1989 Respiratory Medicine vol. 83, 111–118.

Petak, et al., "Partitioning of Pulmonary Impedance: Modeling vs. Alveolar Capsule Approach", 1993, The American Physiological Society, 513–521.

Romero et al., "High–Frequency Characteristics of Respiratory Mechanics Determined by Flow Interruption", 1990, The American Physiological Society, 1682–1688.

Suki et al., "Pseudorandom Signals to Estimate Apparent Transfer and Coherence Functions of Nonlinear Systems: Applications to Respiratory Mechanics", IEEE Transactions on Biomedical Engineering, vol., 39, No., 11, 1142–1151.

Suki et al., "Nonlinearity and Harmonic Distoration of Dog Lungs Measured by Low–Frequency Forced Oscillations", 1991, The American Physiological Society, 69–75.

Suki et al., "Lung Impedance in Healthy Humans Measured by Forced Oscillations from 0.01 to 0.1 Hz", 1989, The American Physiological Society, 1623–1629.

Lutchen et al., "Understanding Pulmonary Mechanics using the Forced Oscillations Technique", 1996, Bioengineering Approaches to Pulmonary Physiology and Medicine, 227–253.

Younes, "A Method for Determining the Pressure–Flow (P–V) Relation During Proportional Assist Ventilation", Abstract 1997.

Magdy, A Method for Estimating Pressure–Volume (P–V) Relation During Proportional Assist Ventilation (PAV), Abstract 1997.

APPARATUS AND METHOD FOR DETERMINING RESPIRATORY MECHANICS OF A PATIENT AND FOR CONTROLLING A VENTILATOR BASED THEREON

CROSS REFERENCE TO RELATED APPLICATIONS

This application claims the benefit of U.S. Provisional Patent Application No. 60/097,490 filed Aug. 21, 1998.

BACKGROUND OF THE INVENTION

1. Field of the Invention

The present invention pertains to a system and method for determining a respiratory condition of a patient and to a system and method for controlling a ventilation system based on the determined condition, and, in particular, to a system and method that non-invasively measures a patient's elastance and resistance and to a ventilator that employs such a method to measure elastance and resistance during ventilation so that the ventilatory assistance provided to the patient by the ventilator is automatically adjusted to suit the needs of the patient.

2. Description of Related Art

The related art will be described with reference to the following patents and other publications, the disclosures of which are hereby incorporated by reference in their entireties into the present disclosure. Throughout the description of the related art, these references will be cited by the first-named author and the year of publication, e.g., Jackson, 1974.

M. Franetzki et al, U.S. Pat. No. 4,051,843 (1977); U.S. Pat. No. 4,022,193 (1977); and U.S. Pat. No. 4,122,839 (1978).

M. M. Grunstein, U.S. Pat. No. 4,802,492 (1989).

P. H. Vooren, U.S. Pat. No. 4,259,967 (1981).

Y. Yoshitsugu, European Published Patent Application 0 521 515 A1 (1993).

P. J. Chowiency, C. P. Lawsom, et al, U.S. Pat. No. 5,233,998 (1993).

Bates, J. H. T., Daroczy, B., and Hantos, Z., "A Comparison of Interrupter and Forced Oscillation Measurements of Respiratory Resistance in the Dog," *Journal of Applied Physiology*, Vol. 72, Iss. 1., pp. 46–52 (1992).

Bates, J. H. T., Decramer, M., Zin, W. A., Harf, A., "Respiratory Resistance with Histamine Challenge by Single-breath and Forced Oscillation Methods," *Journal of Applied Physiology*, Vol. 61, No. 3, pp. 873–80 (1986).

Bates, J. H. T., Baconnier, P., Milic-Emili, J., "A Theoretical Analysis of Interrupter Technique for Measuring Respiratory Mechanics," *Journal of Applied Physiology*, Vol. 64, No. 5, pp. 2204–14 (1988).

Calhoun, Karen H., House, William, et al, "Normal Nasal Airway Resistance in Noses of Different Kinds and Shapes," *Otolaryngology Head and Neck Surgery*, Vol. 103, No. 4, pp. 605–9 (1990).

Chatburn, Robert L., "A New System for Understanding Mechanical Ventilators," *Respiratory Care*, Vol. 36, No. 10, pp. 1123–55 (1991).

Chiang, S. T., Green, J., Gao Y. C., "Determination of Total Respiratory Resistance in Health and Disease by Added External Resistance," *Chest*, Vol. 93, pp. 537–40 (1988).

Chowienczyk, P. J., Lawson, C. P., et al, "A Flow Interruption Device for Measurement of Airway Resistance," *European Respiratory Journal*, Vol. 4, pp. 623–628, (1991).

Daroczy, B., Hantos, Z., "Generation of Optimum Pseudorandom Signals for Respiratory Impedance Measurements," *International Journal of Biomedical Computation*, Vol. 25, pp. 21–31 (1990).

Frank, N. R., Mead, J., Whittenberger, "Comparative Sensitivity of Four Methods for Measuring Changes in Respiratory Flow Resistance in Man," *Journal of Applied Physiology*, Vol. 31, No. 6 (December, 1971).

Green, J., Chiang, S. T., Yang Y. C., "Improved Computation of Respiratory Resistance as Measured by Transiently Increased Resistance," *Medical & Biological Engineering & Computing*, Vol.28, pp. 50–53 (1990).

Gimeno, F., van der Weele, L. Th., "Variability of Forced Oscillation (Siemens Siregnost FD5) Measurements of Total Respiratory Resistance in Patients and Health Subjects," *Annals of Allergy*, Vol. 71, pp. 56–60 (July, 1993).

Hantos, Z., Daroczy, B., Suki, B., "Forced Oscillatory Impedance of the Respiratory System at Low Frequencies," *Journal of Applied Physiology*, Vol. 60, pp. 123–32 (1986).

Jackson, A. C., Milhom, H. T., and Norman, J. R., "A Reevaluation of the Interrupter Technique for Airway Resistance Measurement," *Journal of Applied Physiology*, Vol. 36, No. 2 (December, 1974).

Lutchen, Kenneth, Yang, Kun, Kaczka, David W., "Optimal Ventilation Waveforms for Estimating Low-Frequency Respiratory Impedance," *Journal of Applied Physiology*, Vol. 75, Iss. 1, pp. 478–88 (1993).

Lutchen, Kenneth., Kaczka, David W., Suki, Bela, "Low-frequency Respiratory Mechanics Using Ventilator-driven Forced Oscillations," *Journal of Applied Physiology*, Vol. 75, No. 6, pp. 2549–60 (1993).

Mayewski, Raymond J., Hyde, Richard W., "Measurement of Static Pressure-Volume Relationships of the Lung and Thorax," *The Selective and Comprehensive Testing of Adult Pulmonary Function*, E. Leslie Chusid, ed., Futura Publishing Co., New York (1983).

Morozoff, Paul E., Evans, Ron W., "Real-Time Display of Flow-Pressure-Volume Loops," *Biomedical Instrumentation & Technology* (July/August, 1992).

Neild, J. E., "The Repeatability and Validity of Respiratory Resistance Measured by the Forced Oscillation Technique," *Respiratory Medicine*, Vol. 83, pp. 111–18 (1989).

Petak, F., Hantos, Z., Adamicza, A., "Partitioning of Pulmonary Impedance: Modeling vs. Alveolar Capsule Approach," *Journal of Applied Physiology*, Vol. 75, No. 2, pp. 513–521 (1993).

Romero, P. V., Sato, J., Shardonfsky, F., "High-frequency Characteristics of Respiratory Mechanics Determined by Flow Interruption," *Journal of Applied Physiology*, Vol. 69, No. 5, pp. 1682–88 (1990).

Suki, Bela, Lutchen, Kenneth R., "Pseudorandom Signals to Estimate Apparent Transfer and Coherence Functions of Nonlinear Systems: Applications to Respiratory Mechanics," *IEEE Transactions on Biomedical Engineering*, Vol. 39, No. 11 (November, 1992).

Suki, B., Hantos, Z., "Nonlinearity and Harmonic Distortion of Dog Lungs Measured by Low-Frequency Forced Oscillations," *Journal of Applied Physiology*, Vol. 71, pp. 69–75 (1991).

Suki, B., Peslin, R., Duvivier, C., "Lung Impedance in Health Humans Measured by Forced Oscillations from 0.01 to 0.1 Hz," *Journal of Applied Physiology*, Vol. 67, No. 4, pp. 1623–29 (1989).

To understand how a machine can be controlled to replace or supplement the natural function of breathing, it is necessary to understand the mechanical nature of the respiratory system. The study of the mechanical behavior of the respiratory system requires analyzing the elastance and resistance properties of the patient's pulmonary system, which includes the airways, lung and thoracic cage. In clinical practice, respiratory resistance $R_{rs}$ and elastance $E_{rs}$ are essential information necessary to describe the behavior of the lung and the chest wall in health and disease states, and, in particular, to describe characteristics of that behavior, such as inspiratory vital capacity (IVC) and the forced expiratory volume in one second (FEV1). Furthermore, the use of state-of-the-art mechanical ventilation techniques, such as proportional assist ventilation (PAV), which is disclosed in U.S. Pat. Nos. 5,107,830 and 5,044,362 both to Younes, the contents of which are also incorporated herein by reference, requires knowledge of the patient's respiratory resistance and elastance.

Measuring the respiratory resistance and elastance of a spontaneously breathing patient is not a simple task. Conventional techniques for measuring resistance and elastance are somewhat invasive in that they are performed in a clinical or hospital setting and require placing a device for measuring esophageal pressures, such as an esophageal balloon, within the patient. Therefore, $R_{rs}$ and $E_{rs}$ are typically not measured on a routine basis. In order to perform these measurements more routinely, there is a need for an efficient and reliable technique that is as non-invasive as possible and requires little or no patient cooperation for spontaneously obtaining $R_{rs}$ and $E_{rs}$, especially inspiratory $R_{rs}$ and $E_{rs}$.

Respiratory mechanics takes into consideration the forces, displacement, rate of change (first time derivative) of displacement, and acceleration (second time derivative) of displacement. In respiratory physiology, force is measured in terms of pressure P, displacement is measured as volume V, rate of change of displacement is measured as flow $\dot{V}$ (first time derivative), and acceleration of displacement is measured as the rate of change of flow $\ddot{V}$ (second time derivative of displacement). Particularly relevant to assisted breathing is the pressure P necessary to cause a flow of gas $\dot{V}$, thereby increasing the volume of the lungs V against the inertial force of the respiratory system caused by the rage of change of flow $\ddot{V}$.

Over the course of a breathing cycle, i.e., one inspiration and one expiration, pressure P(t) (typically measured in cm $H_2O$), volume V(t) (typically measured in liters), flow $\dot{V}$(t) (typically measured in liters/second) and rate of change of flow $\ddot{V}$(t)(typically measured in liters/second$^2$) all change with time. The total force, i.e., pressure, necessary to expand the lungs and chest wall must overcome the following three different forces: inertial force, resistive force, and elastic recoil force, all of which are developed by the respiratory system and oppose its expansion. A mathematical model, i.e., the equation of motion, for the respiratory system describes the relation among the pressure, flow and volume as follows:

$$P_{aw}(t)+P_{mus}(t)=I\ddot{V}(t)+R_{rs}\dot{V}(t)+E_{rs}V(t) \qquad (1)$$

In this equation, $P_{aw}$(t) is the ventilator pressure applied at the airway opening. Muscle pressure $P_{mus}$(t) is the imaginary transrespiratory pressure (airway pressure—body surface pressure) generated by the ventilatory muscles to expand the thoracic cage and lungs. Muscle pressure $P_{mus}$(t) is not directly measurable.

Elastic force $E_{rs}V(t)$ is the force with which the respiratory system attempts to recoil after deflation. The elastic force is generated by the lung and thorax elastic supporting structures. $E_{rs}$ is defined as the change in distending pressure per change in volume and is the reciprocal of compliance and is expressed in units of cm $H_2O$/liter. The total static respiratory recoil volume pressure $P_{rs}$ is given by the sum of pressure $P_l$ developed across the lungs and pressure $P_{cw}$ developed across the chest wall:

$$P_{rs}=P_l+P_{cw}. \qquad (2)$$

Because volume change $V_{rs}$ in the respiratory system is given by the sum of volume change $V_l$ in the lungs and volume change $V_{cw}$ in the chest wall, the total respiratory elastance $E_{rs}$ is given by the sum of lung elastance $E_l$ and chest wall elastance $E_{cw}$:

$$E_{rs}=E_l+E_{cw}. \qquad (3)$$

Total respiratory elastance $E_{rs}$ is dependent on factors such as lung size, the sex of the patient, the growth and aging of the patient, the resting positions of the lungs in the thorax, and gravitational (positional) effects. The dynamic elastance has a marked deviation from the static elastance because of uneven time constants in the airways and lung parenchyma (See Mayewski, 1983).

Resistive force $R_{rs}$ $\dot{V}(t)$ is the force exerted by the movement of gas and tissue elements in the lungs and thorax that oppose movement of the lungs and thorax. Total respiratory resistance $R_{rs}$ is determined by dividing the pressure gradient between the airway opening and the body surface of the chest cage required to overcome non-elastic and non-inertial factors by flow. The pressure gradient used in the measurement of $R_{rs}$ includes the sum of the pressure necessary to move air through the airways (which gives $R_{aw}$), the pressure necessary to change the shape of the lung tissues (which gives tissue viscous resistance $R_{visc}$) and the pressure necessary to move the chest wall and the diaphragm (which gives $R_{wall}$). $R_{rs}$ is expressed in units of cm $H_2O$/(liter/second), or cm $H_2O\cdot$sec/liter, and is given by the following formula:

$$R_{rs}=R_{aw}+R_{visc}+R_{wall} \qquad (4)$$

Inertial force $I\ddot{V}(t)$ is the force introduced by the inertial property of the respiratory system. It is proportional to the rate of change of flow. Under normal circumstances, this force is usually negligible. However, the effect of the inertial force increases with increases in the patient's ventilation rate.

Equation (1) provides a dynamic model in which pressure, flow and volume are all measured relative to their baseline values (i.e., their values at the end of expiration). The pressure that causes inspiration is measured as the change in airway pressure above positive end-expiratory pressure (PEEP). The volume is measured as the change in lung to volume above the functional residual capacity (FRC). Flow is measured with respect to its end-expiratory value, which is usually zero.

The parameters in Equation (1) are not necessarily constant. In fact, the mechanical behavior of the respiratory system has been characterized as nonlinear. Almost every mechanical aspect of lung behavior can exhibit nonlinear characteristics. The pressure-area behavior of the airway walls, the pressure-volume behavior of the lung parenchyma and the pressure-flow behavior of the airway gas are all well documented as being nonlinear. The variables known to change resistance and elastance are very complex, including flow rate, lung volume, points in the ventilatory cycle and ventilatory rate. However, the dominant factors in the non-linear properties of $R_{rs}$ and $E_{rs}$ are flow and volume, respectively. Thus, $R_{rs}$ can be expressed approximately as a function of flow, $R_{rs}(\dot{V}(t))$. Likewise, $E_{rs}$ can be expressed approximately as a function of volume, $E_{rs}(V(t))$. As a further simplification, the following first order equations may be used to reflect the nonlinear factors:

$$E_{rs} = E_{rs0} + E_{rs1}V(t) \quad (5)$$

$$R_{rs} = R_{rs0} + R_{rs1}\dot{V}(t) \quad (6)$$

where $E_{rs0}$ and $R_{rs0}$ are constant terms and $E_{rs1}$ and $R_{rs1}$ are first-order terms. With this approximation, the equation of motion can be expressed in the first order as follows:

$$P_{aw}(t) + P_{mus}(t) = (E_{rs0} + E_{rs1}V(t))V(t) + (R_{rs0} + R_{rs1}\dot{V}(t))\dot{V}(t) + I\ddot{V}(t) \quad (7)$$

Many other models have been developed in recent years, including a sophisticated physiological model, that reflects tissue viscoelasticity as well as the inertial effects of the airways and branching networks. However, the use of non-linear models precludes application of many powerful concepts typically employed in a clinical investigation of respiratory mechanics, such as the use of frequency-domain analysis, Bode diagrams and multilinear regression. In most cases, it is acceptable to consider $R_{rs}$ and $E_{rs}$ as constant and to use the following two-element linear model:

$$P_{aw}(t) + P_{mus}(t) = E_{rs0}V(t) + R_{rs0}\dot{V}(t) \quad (8)$$

A study of respiratory mechanical properties is an important area of interest to respiratory care professionals. In accordance with the analysis of mechanics and breathing, respiratory mechanics can be assessed if it is possible to measure $P_{aw}(t)$, $\dot{V}(t)$ and $P_{mus}(t)$. The first two variables are easily measured by means of sensors located at the airway opening. However, there is believed to be presently no known direct method of non-invasively measuring $P_{mus}(t)$ under dynamic conditions.

There are other situations in which it is it important to know the patent's respiratory mechanics. For example, in order to implement proportional assist ventilation, which is a synchronized partial ventilation method that amplifies patient respiratory effort to deliver pressure to the patient in proportion to the patient's instantaneous effort, a knowledge of patient's respiratory mechanics is required. The respiratory mechanics, such as resistance and elastance, are used in a PAV system to determine the proper level of flow and volume support. For a ventilator supported patient, such parameters constantly vary because of different physical and pathological conditions. Therefore, it is important to be able to continuously or periodically determine these parameters while minimizing the obtrusiveness of the measurements required to do so.

In short, PAV requires accurate resistance and elastance values to maintain optimal flow and volume support so that the pressure support truly accommodates the patient's breathing effort. Compared with other ventilation modes, PAV requires detailed information on respiratory mechanics and more interaction with the patient. Such interaction is preferably performed on an ongoing basis, because, as noted above, respiratory mechanics are variable for most patients.

Many noninvasive respiratory mechanics measurement techniques have been developed. In general, these measurement techniques can be divided into the following five categories: interrupter/occlusion, variable external resistance, time constant, multi-linear regression and forced oscillation. However, these conventional clinical techniques for determining resistance and elastance are cumbersome and cannot be performed easily on a ventilator supported patient. Furthermore, several of these techniques require manually implemented procedures and cannot be performed using most ventilators, especially ones that exhibit system leak.

The interrupter/occlusion method estimates the mean alveolar pressure. See Jackson, 1974. This measurement method entails providing a rapid occlusion, e.g., approximately 0.1 second, in the breathing circuit during a normal breathing cycle. This technique assumes that during the occlusion, the alveolar pressure and the pressure at the airway opening equilibrate so rapidly that the net movement of the rib cage and the diaphragm does not change intrapleural pressure appreciatively, although continued respiratory effort is still present. The pressure measured at the airway opening immediately after equilibration is used to estimate the alveolar pressure just prior to the occlusion.

The interrupter/occlusion method is the most common clinical practice for estimating lung elastance. The occlusion is usually performed at the beginning of an exhalation. Upon providing the occlusion, the pressure at the airway opening increases and plateaus in about 250 ms, when the respiratory muscles are completely relaxed. The plateau pressure equilibrates with the respiratory elastic recoil force. Because the occlusion is provided at the beginning of exhalation, the total air volume in the respiratory system equals to the tidal volume $V_{tidal}$ plus the functional residual capacity. The elastance $E_{rs}$ can be determined if pressure and volume are known.

For a non-leak system, clinicians manually block the exhalation path using their hands, an exhaustion valve or a shutter. In an open circuit system, however, the system leak, e.g., exhalation or exhaust port, is typically located very close to the patient's airway. Therefore, it is not practical to insert a shutter between the leak and the airway opening. A commercially available flow interruption device is taught by U.S. Pat. No. 5,233,998 for measuring airway resistance, but not total respiratory resistance, $R_{rs}$. This technique is difficult to implement on a ventilators with a system leak for the reasons noted above, namely it is not practical to provide the occlusion between the leak and the patient's airway.

The variable external resistance technique is reported to measure $R_{rs}$ by using a rapid and brief increase in external resistance ($R_{ext}$). See M. Franetzki, 1977; Chiang, 1988; and Green, 1990. This measurement method is based on the assumption that while the external resistance is in series with $R_{rs}$, the changes in muscle pressure ($P_{mus}$) and elastic force are negligible. This technique, however, is incomplete in that it ignores the possible effect caused by the inertial factor of the respiratory system. It is also difficult to incorporate this technique into a ventilator because it requires measuring linear resistance, which cannot be done readily using conventional ventilators.

The time constant method is used to estimate resistance and elastance during an expiratory phase by examining how exhalation decays. See, e.g., Grunstein, U.S. Pat. No. 4,802, 492, 1989. However, studies have shown that inspiratory resistance and elastance values are different from the expiratory resistance and elastance values. Therefore, this technique is not well suited to measure or estimate inspiratory resistance and elastance.

The multi-linear regression method is used to estimate resistance of an anesthetized patient whose muscle pressure is eliminated. Accordingly, this technique is not applicable for an active patient.

The forced oscillation technique applies an oscillated pressure at the patient's airway opening. It has become a very popular means for scientists to study the respiratory system. Some studies suggest that the oscillation frequency should be set around 6–7 Hz because that is the resonant frequency of the respiratory system in humans. See Frank, 1971. Studies have also reported that reliable estimates of resistance cannot be expected at frequencies lower than 2–4 Hz, especially for patients whose breathing pattern is relatively rich in harmonics, such as vigorously breathing children or an obstructed patient. See, e.g., Daroczy, 1990 and Hantos, 1986.

In clinical applications, due to the expensive and bulky instrument required, this technology was not widely used until Siemens introduced the Siregnost FD-5 portable oscillometer in the early 1980's. See Gimeno, 1993. After a clinical study, Neild et al. (1989) proved the repeatability and validity of a derived measurement of $R_{rs}$ obtained with the Siregnost FD-5. One of the reasons the forced oscillation technique has become a widely used method for measuring the total respiratory resistance is the fact that the patient's cooperation can be kept at minimum. Most forced oscillation devices use loudspeakers in enclosures or linear motor pumps as a high frequency pressure oscillation source to produce controlled perturbations in the airway. In addition, the existing forced oscillation technique use a sequenced pressure oscillation during the patient's entire inspiration phase. Therefore, the conventional forced oscillation technique is not practical for ventilator supported patients on an ongoing basis.

SUMMARY OF THE INVENTION

It is an object of the invention is to provide a non-invasive apparatus and method for measuring resistance and/or elastance that is readily performed on a ventilator supported patient, especially in conjunction with ventilator having a system leak, that overcomes the disadvantages associated with the conventional devices and techniques.

A further object of the invention is to provide a system and method that automatically adjusts the settings of a ventilator to adapt to the continuously changing mechanical parameters of the patient and to follow those parameters without continuous action by the operator and/or patient.

A still further object of the invention is to provide a system and method that implements a noninvasive technique for automatically evaluating a pressure-flow relation, a pressure-volume relation, or both for a ventilator supported patient.

Another object of the invention is to provide the above system and method on conventional pressure or volume ventilator without requiring significant structure changes, and that is capable of working with known and/or unknown leaks in the ventilator circuit.

Yet another object of the invention is to provide a system and method that non-invasively and spontaneously monitors the total respiratory elastance $E_{rs}$ and/or total respiratory resistance $R_{rs}$ of a ventilator supported patient with little or no patient cooperation.

These objects are achieved by providing an adaptive proportional assist ventilation (APAV) system that monitors a ventilator supported patient's respiratory mechanics and adaptively adjusts the support being provided to the patient in accordance therewith. The APAV system includes a ventilator that delivers a therapeutic pressure to the respiratory system of the patient; a respiratory mechanics monitoring system that, in conjunction with the ventilator, non-invasively determines the resistance and/or elastance of the patient's respiratory system; and a control unit that controls the ventilator to adjust the therapeutic pressure provided to the patient in accordance with the resistance and the elastance determined by the resistance and the elastance monitoring system.

These objects are also achieved by providing a method for monitoring a ventilator supported patient's respiratory mechanics and adaptively adjusting the support being provided to the patient in accordance therewith. The method includes (a) controlling a ventilator to deliver a therapeutic pressure to the respiratory system of the patient; (b) detecting a resistance and/or an elastance of the respiratory system of the patient; and (c) controlling the ventilator to adjust the therapeutic pressure based on the detected resistance and/or elastance.

The APAV technique of the present invention is a type of PAV system. However, unlike PAV, whose flow and volume control gains remain constant throughout the therapy delivery process, APAV allows the PAV system to automatically adjust the flow and volume gains to control the flow and volume assist provided by the ventilator to best support the patient on an ongoing basis. More specifically, the present invention enables PAV's flow and volume gains to be adaptively adjusted according to the patient's current respiratory resistance and elastance, respectively. This is accomplished in the present invention by automatically and non-invasively evaluating the patient's resistive and elastic recoil properties during an inspiratory and/or expiratory phase in a manner that is substantially unnoticeable to the patient and that requires no cooperation from the patient or operator assistance. With APAV, the operator need only to set the prescribed assistance rate (0–100%) without having to first determine elastance and resistance using the conventional techniques discussed above.

According to the principles of the present invention, automatically non-invasively evaluating the respiratory pressure-flow relation (respiratory resistance, $R_{rs}$) of a patient is accomplished using a forced single oscillation (FSO) technique in which at least one pressure oscillation is superimposed on the therapeutic pressure that is delivered by a ventilator to the patient at a specified time during the inspiratory phase. In an exemplary embodiment of the present invention, at least one sinusoidal pressure oscillation having a frequency in a range of 3–10 Hz and a pressure of 2–10 cm $H_2O$ is superimposed on the pressure delivered to the patient. The FSO technique of the present invention generates small instantaneous airway pressure and flow variations in the therapeutic pressure delivered to the patient by the ventilator. These local changes, which reflect the responses of the respiratory system to the pressure oscillation, are processed by the present invention to determine the pressure-flow relation (respiratory resistance, $R_{rs}$) of the patient's respiratory system.

According to the principles of the present invention, automatically non-invasively evaluating the respiratory pressure-volume relation (elastance, $E_{rs}$) for a patient is accomplished using a pneumatic occlusion method (POM) in which a controlled pressure is applied at the patient's airway opening for a brief period of time. In an exemplary embodiment of the present invention, the controlled pressure is applied for a duration of up to 0.4 seconds. The controlled pressure at the patient's airway opening is initiated at the start of exhalation and pneumatically occludes the patient's exhalation flow. While the flow is pneumatically maintained at zero, the applied pressure reaches its equilibration state (or pressure plateau), which is equivalent to the elastic recoil force from the respiratory system. Meanwhile, the volume remains at the same level and is equivalent to the inspiratory tidal volume plus the functional residual capacity (FRC). The pressure plateau, tidal volume and airway pressure at the end of expiration (when the lung volume equals FRC) are measured and used by the present invention to determine the respiratory pressure-volume relation, i.e., respiratory elastance $E_{rs}$.

The present invention contemplates that one or both of the FSO method and POM discussed above are incorporated into the APAV system. It is to be understood, however, that the FSO method or POM can be used in other applications where it is desirable to know $E_{rs}$ or $R_{rs}$ independent of a pressure support system.

In summary, the present invention provides a noninvasive technique to determine $E_{rs}$ and/or $R_{rs}$ spontaneously and automatically for ventilator-supported patients. Such a technique can be implemented on a wide variety of pressure or volume ventilators without the need for significant structure changes. For ventilators that have embedded microprocessors, the teachings of the present invention can be implemented merely by providing the appropriate software to the existing microprocessor. Furthermore, the techniques of the present invention can be implemented in ventilators that have a leak.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EXEMPLARY EMBODIMENTS OF THE INVENTION

One embodiment of the present invention is referred to as an adaptive proportional assist ventilation (APAV) device and method because it enables the gains that are used in a PAV device to be automatically altered based on the current conditions of the patient. Thus, the present invention permits PAV to be performed based on the present state of the patient, as opposed to being based on a condition of the patient measured some time ago in a hospital or clinic.

Figure 1:
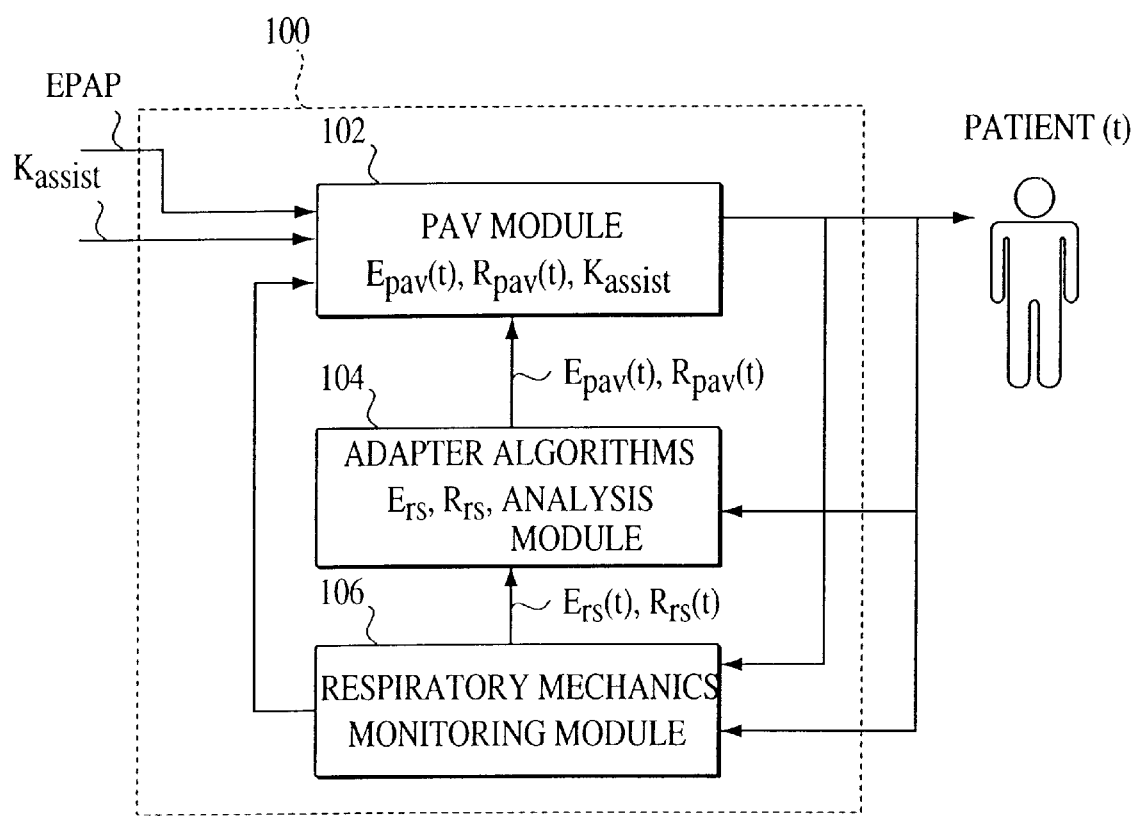
FIG. 1 is a schematic diagram of an APAV system according the principles of the present invention.

As shown in FIG. 1, APAV system 100 of the present invention includes the following three modules: a PAV module 102, an adapter module 104, and a patient's respiratory mechanics monitoring module 106. Adapter module 104 can be implemented in hardware and/or software. APAV is initiated by setting a prescribed assistance rate $K_{assist}$, which represents the degree of the ventilator's accommodation for the patient's breathing effort, and the EPAP, which is the patient's expiratory positive airway pressure.

Adapter module 104 obtains the patient's respiratory mechanics ($E_{rs}$ and/or $R_{rs}$) from monitoring module 106 and the patient's airway pressure and flow signals and adjusts the PAV settings ($E_{pav}$, $R_{pav}$) so that PAV module 102 delivers a pressure to the patient that is proportional to the patient's muscle pressure during the inspiratory phases. In an exemplary embodiment of the present invention, adapter module 104 averages elastance and resistance measurements over a plurality of patient breaths to account for the effects of noise during the measurement. The rate of adaptation is controlled by a gain factor (0–1) so that APAV provides stable pressure support despite disturbances, such as large transitory patient efforts, noise, and severe nonlinear lung behavior. More details of adapter module 104 are discussed below with reference to FIGS. 8 and 9.

As noted above, with the APAV technique of the present invention, there are two settings for the operation of the ventilator, namely, the assistance rate and the expiratory positive airway pressure (EPAP). The assistance rate indicates the percentage of the patient's elastance and resistance which should be allocated to the ventilator. The ventilator pressure output is controlled automatically as the patient's demand changes. Other than conventional clinical procedures for providing ventilator support, no special caution or patient cooperation is required in order to practice the invention.

For ventilators that have a leak, the patient's flow is estimated by employing leak estimation technology. U.S. Pat. Nos. 5,148,802 and 5,433,193 both to Sanders et al. and U.S. Pat. Nos. 5,313,937, 5,632,269, and 5,803,065 all to Zdrojkowski et al., the contents of all of which are incorporated herein by reference, disclose techniques for estimating leaks in a ventilation system. In the case of a severe unknown leak, the flow estimation may have an error. Such an error will affect the accuracy of respiratory mechanics evaluations performed by respiratory mechanics monitoring module 106. However, PAV module 102 also uses estimated flow for its allocations of flow and volume support ($R_{rs} \dot{V}$, $E_{rs} V$). Analysis shows that the aforementioned errors in the respiratory mechanics $E_{rs}$ and $R_{rs}$ caused by a flow estimation error offset the errors caused by the flow estimation in the PAV module when calculating the flow and volume support. Therefore, errors in flow estimation due, for example, to an unknown leak, have limited affect in the final results of the APAV system of the present invention. For this reason, APAV, unlike PAV alone, provides an advantage in self-correcting minimizing leak estimation errors.

The techniques of the present invention for non-invasively determining the patient's resistance $R_{rs}$ and elastance $E_{rs}$ are discussed below. These techniques are implemented by monitoring module 106. The description set forth above and the block diagram of FIG. 1 are applicable to both techniques. It is to be understood however, that the following techniques for determining elastance $E_{rs}$ and resistance $R_{rs}$ and can be incorporated into APAV system 100 of the present invention or used alone, i.e., without PAV module 102 and/or adapter module 104, whenever it is desirable to know elastance $E_{rs}$ and/or $R_{rs}$.

The first technique of the present invention is called forced single oscillation, or FSO and is used to determine a patient's respiratory resistance $R_{rs}$. Forced single oscillation involves generating a single pressure oscillation and imposing that oscillation on the pressure delivered to the patient. Several separate, distinct and unrelated oscillations can be developed and imposed on the pressure provided to the patient during the insipratory phase of the breathing cycle to increase the number of resistance measurements taken during each breathing cycle. For example, plural (e.g., two or more) separate oscillations are used if the respiratory system needs to be treated as non-linear; otherwise, one oscillation suffices.

It should be noted that conventional forced oscillation techniques apply a continuous series of oscillations to the patient. This is necessary because the conventional techniques performs a spectral analysis of resulting pressure and flow measurements and obtains a continuous average. This conventional technique, however, tends to make the patient uncomfortable because it imposes a continuous series of pressure oscillations on the patient's respiratory system. The FSO technique of the present invention, on the other hand, provides a single pressure oscillation on the patient, which typically takes place too fast for the patient to notice or to interrupt the therapy being provided to the patient. As noted above, in a further embodiment, a two or more individual oscillations are imposed on the patient during the inspiratory phase of the respiratory cycle. In this embodiment the individual oscillations are spaced apart to measure the resistance at different flow rates, which is especially beneficial for non-linear systems. The present invention contemplates that the individual pressure oscillations are produced by the pressure control system in a ventilator. Therefore, no special mechanisms, such as speakers or linear motor pumps, are required. The pressure oscillation is achieved by superimposing a pressure oscillation signal on top of the pressure support provided by the ventilator. The instantaneous airway pressure change due to the FSO induces a corresponding flow change.

Figure 2A:
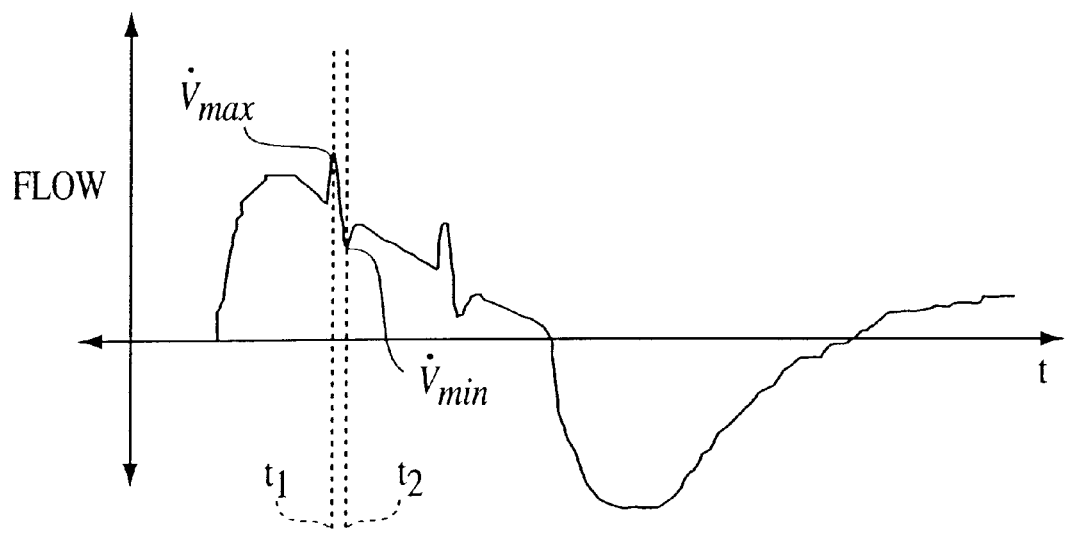
FIGS. 2A and 2B illustrate pressure and flow waveforms, respectively, describing the operation of the forced single oscillation technique of the present invention.
Figure 2B:
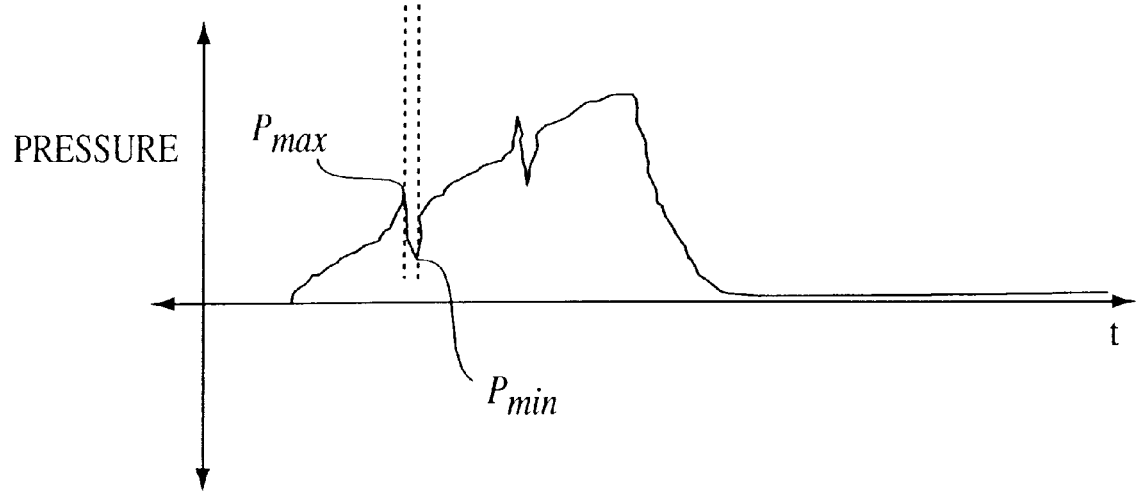
Figure 3:
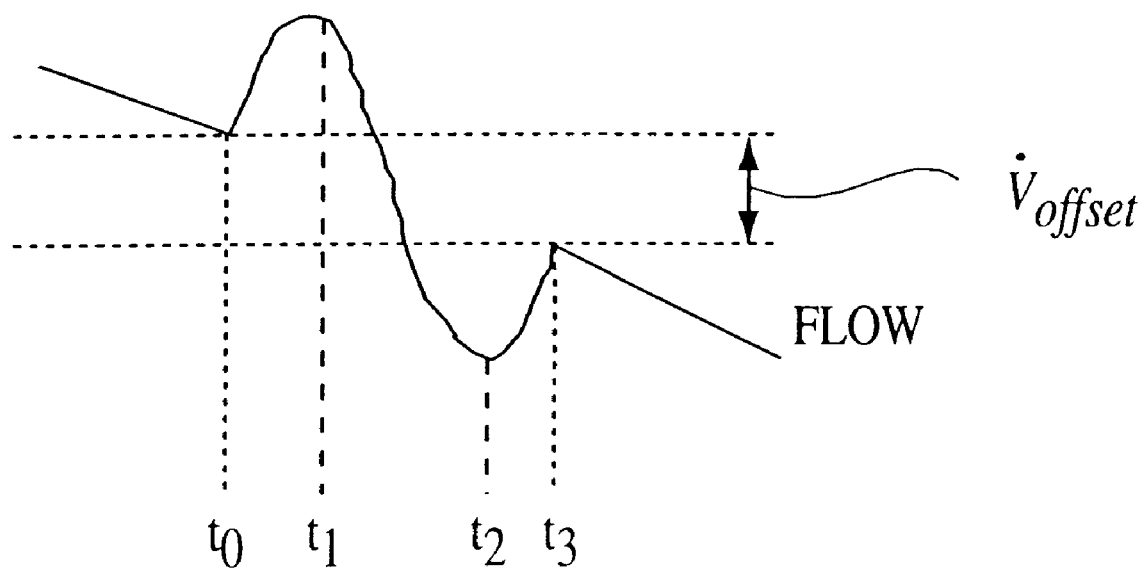
FIG. 3 illustrates a modification of the flow waveform shown in FIG. 2A when the patient's elastance and muscle pressure are not negligible.

FIGS. 2A–2B illustrate flow and pressure waveforms, respectively, under the combination of FSO and PAV. More specifically, the waveform in FIG. 2B illustrates the airway pressure $P_{aw}$ provided to the patient that is obtained by combining FSO and PAV, and FIG. 2A is the flow to and from the patient as a result of the application of the pressure oscillation on the pressure provided to the patient. It should be noted that the flow and pressure waveforms in FIGS. 2A–2B are provided for the purposes of illustration, and are not intended to accurately represent the flow and pressure waveforms of an actual patient. FIG. 3 shows a magnified portion of the flow waveform of FIG. 2B during the FSO technique of the present invention.

As shown in FIGS. 2A–3, the flow resulting from the FSO reaches a maximum and a minimum peak value at times $t_1$ and $t_2$, respectively. The duration between $t_1$ and $t_2$ is approximately one half period of the oscillation. It should be noted that there is a slight delay between the application of the pressure oscillation on the pressure provided to the patient, FIG. 2B, and the oscillation in the patient's flow as a result of the oscillation, FIG. 2A. This is so because the patient's respiratory system cannot respond instantaneously with the application of the pressure oscillation. Therefore, the maximum and minimum peak flow value at times $t_1$ and $t_2$ are slightly delayed from the maximum and minimum peak pressure values of the FSO. Because this delay is relatively small, it is not illustrated in FIGS. 2A and 2B.

The effectiveness of the FSO technique is based on the following two conditions being satisfied: first, the oscillation must be fast enough so that patient's effort change is negligible, and, second, the amplitude of the oscillation should be large enough to obtain a reasonably good signal-to-noise ratio (S/N) in the flow measurement, but small enough to avoid any noticeable discomfort on the part of the patient or upset of the ventilator's flow triggering. The patient's respiratory effort, ventilator support and FSO can be understood as three combined sources for a respiratory system. At the FSO's flow peak ($t_1$), the effect of respiratory inertial force is minimized, because the rate of flow change is small. It is to be understood that the pressure peak does not necessarily occur at the same time as the flow peak.

If the FSO is fast enough, the changes of volume V(t) and muscle pressure $P_{mus}$(t) between $t_1$ and $t_2$ are assumed to be negligible so that:

$$V(t_1)=V(t_2), \tag{9}$$

and $$P_{mus}(t_1)=P_{mus}(t_2) \tag{10}$$

$R_{rs}$ is then derived as follows:

$$R_{rs} = \frac{P_{aw}(t_1) - P_{aw}(t_2)}{\dot{V}(t_1) - \dot{V}(t_2)} \tag{11}$$

Figure 4:
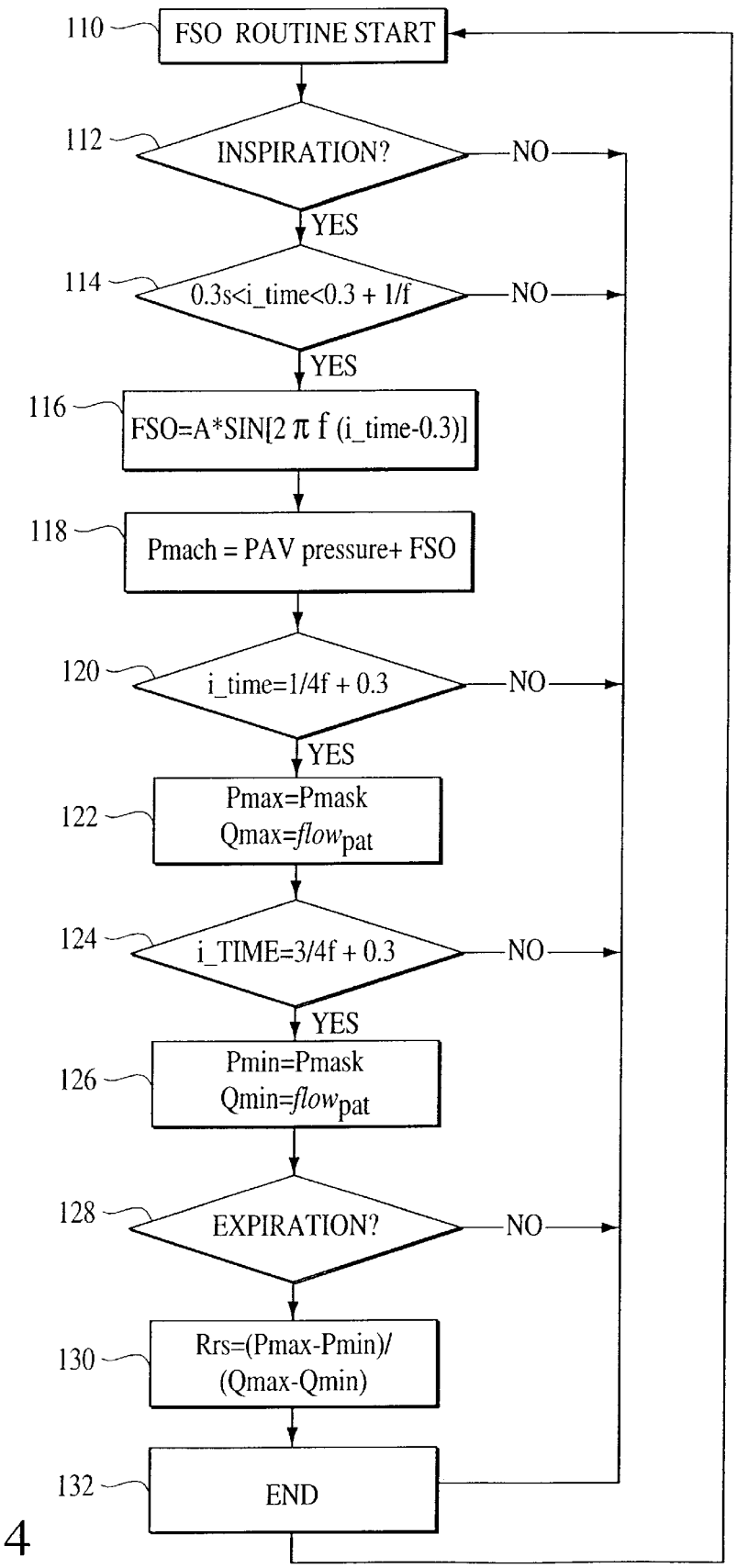
FIG. 4 is a flow chart of illustrating the forced single oscillation technique for determining respiratory resistance according to the principles of the present invention.

FIG. 4 illustrates an algorithm used to determine $R_{rs}$ according to the above described technique. This algorithm is preferably repeatedly executed by the processor in respiratory mechanics monitoring module 106. The FSO routine begins in step 110 and advances to step 112 where the system determines if the patient is currently in the inspiratory phase of a respiratory cycle using any appropriate conventional technique. The pressure oscillation is only applied to the patient during the inspiratory phase. If the patient is not in the inspiratory phase, the routine ends (step 132) and the repeats beginning at step 110. If the patient is in the inspiratory phase, the routine advances to step 114 and determines if a sufficient time has elapsed from the beginning of inspiration to initiate an oscillation and if there is sufficient time left in the inspiration to provide the oscillation. In other words, step 114 specifies the window of time in which the single oscillation is provided to the patient.

In the illustrated embodiment, the current inspiratory time (i_time) is selected to be greater than 0.3 sec from the onset of inspiration in order for the oscillation to be superimposed on the inspiratory pressure. The 0.3 sec delay is chosen to allow the patient's muscles time to transition to the inspiratory phase from the expiratory phase and to maximize the likelihood that the oscillation is provided during the peak inspiratory flow, which occurs shortly after the onset of inspiration. In this embodiment, the oscillation is also applied before the current inspiratory time exceeds 0.3 sec+1/f, where f is the frequency of the oscillation, to ensure that there is sufficient time during the inspiratory phase in which to apply the oscillation.

It is to be understood that the start point (0.3 sec after the onset of inspiration) and the ending point (0.3+1/f) of the time frame in which the oscillation is applied to the patient can vary over a range of values, so long as the oscillation is provided during the inspiratory phase, and preferably during the portion of the inspiratory phase when inspiratory flow is at or near a peak. Furthermore, techniques other than the above described time-based control method for controlling the time of application of the oscillation are contemplated by the present invention. For example, the inspiratory flow rate or volume can be used as a trigger to cause the oscillation to be superimposed on the pressure applied to the to patient by applying the oscillation when the inspiratory flow rate reaches a certain value and/or when the inspiratory volume reaches a certain amount. Preferably, these amounts are selected such that the pressure oscillation is provided during the portion of the inspiratory phase when inspiratory flow is at or near a peak.

If the current inspiratory time is within the time period set forth in step 114, the routine proceeds to step 116. Otherwise, the routine repeats. In step 116, the force single oscillation FSO is calculated as follows:

$$FSO = A \sin(2\pi f (i\_time - 0.3)), \quad (12)$$

wherein A is a constant. The oscillation is applied to the positive airway pressure being provided to the patient by the PAV module in step 118, so that the pressure output by the ventilator Pmach is the sum of the PAV pressure and the FSO.

Next, the maximum pressure and flow are measured in steps 120 and 122 and the minimum pressure and flow are measured in steps 124 and 126. More specifically, in step 122, the routine determines whether the inspiratory time (i_time) is at a time corresponding to ¼f+0.3 after the onset of inspiration, which is the time when the flow resulting from the FSO is a maximum and corresponds to time $t_1$ in FIGS. 2A–3. If so, the maximum pressure (Pmax) and maximum flow (Qmax) are measured at the patient in step 122. If not, the routine repeats via steps 132 and 110. The pressure and flow measured in step 122 are considered to be the maximum pressure (Pmax) and the maximum flow (flow$_{max}$), which correspond to $P_{aw}(t_1)$ and $\dot{V}(t_1)$, respectively, in equation (11).

In step 124, the routine determines whether the inspiratory time (i_time) is at a time ¾f+0.3 after the onset of inspiration, which is the time when the flow resulting from the FSO is at or near a minimum and corresponds to time $t_2$ in FIGS. 2A–3. If so, the minimum pressure (Pmin) and flow (Qmin) are measured at the patient in step 126. If not, the routine repeats via steps 132 and 110. The pressure and flow measured in step 126 are considered to be the minimum pressure (Pmin) and the minimum flow (flow$_{min}$), which correspond to $P_{aw}(t_2)$ and $\dot{V}(t_2)$, respectively, in equation (11). The value 0.3 sec is used in steps 124 and 126 because the FSO pressure oscillation is delayed from the onset of inspiration by 0.3 sec. Therefore, the measurement time must also be delayed by 0.3 sec from the onset of inspiration. It should be understood that whatever time delay is imposed before the start of the pressure oscillation, the same time delay should be accounted for when measuring the pressure and flow resulting from the oscillation.

After obtaining the maximum pressure and flow in step 122 and the minimum pressure and flow in step 126, the routine then determines in step 128 whether the patient is in the expiratory phase of the respiratory cycle. If so, the routine determines the patient resistance $R_{rs}$ in step 130 based on the pressure and flow measurements taken in steps 122 and 126. It is preferable to make this calculation during the expiratory phase to reduce the computational burdens on the ventilator. It should be understood, however, that this calculation can be made during the inspiratory phase as well. The routine then advances to step 132 and repeats beginning at step 110. Thus, the routine illustrated in FIG. 4 repeatedly determines the patient's resistance characteristic without imposing any additional burdens on the patient or caregiver and does so in a manner that minimizes the disturbance in the therapy provided to the patient and minimizes the likelihood that the patient will notice that the measurement is being made.

It should be understood that the routine illustrated in FIG. 4 can be performed during every patient breath or at a selected breathing frequency, such as every $5^{th}$ or $10^{th}$ breath. Alternatively, the FSO technique can be performed based on the elapse of time, such as once every 5 or 10 minutes, depending on the need to continuously update the PAV module or otherwise output the patient's current resistance. Also, it should be understood that techniques other than those described above and illustrated in steps 120–126 to measure the maximum and minimum peak values resulting from the FSO can be used in the present invention. Steps 120–126 describe a time based method to determine when to measure the patient's pressure and flow to capture the maximum and minimum flow and pressure values. However, any technique that can capture the peak and trough in the pressure and flow following the application of the FSO can be used in the present invention. For example, pressure and flow data can be continuously obtained or sampled and computer algorithms, such as peak detectors, can be used to identify the peak and trough in the pressure and flow following the application of the FSO.

If the FSO's frequency is lower than 5 Hz or if the patient has a vigorous respiratory effort, the conditions set forth above may be more difficult to satisfy. FIG. 3 shows an FSO flow waveform when the elastance and $P_{mus}$ are not negligible. During an FSO ($t_0 < t < t_3$), the flow baseline drifts by a baseline offset flow $\dot{V}_{offset}$. Therefore, the peak-to-peak flow change is not induced by the FSO alone. This baseline offset flow should be taken into account in calculating peak-to-peak flow change. If the baseline offset between $t_1$ and $t_2$ is estimated to be half of the offset during the complete cycle, equation (11) above is modified as follows:

$$R_{rs} = \frac{P_{aw}(t_1) - P_{aw}(t_2)}{\dot{V}(t_1) - \dot{V}(t_2) - \dfrac{\dot{V}_{offset}}{2}} \quad (13)$$

where $$\dot{V}_{offset} = \dot{V}(t_0) - \dot{V}(t_3) \quad (14)$$

The resistive properties of respiration are normally nonlinear. Therefore, two separate FSO's are preferably imposed during an inspiration, as shown in FIG. 1, in order to reflect the first-order flow dependency of $R_{rs}$, wherein:

$$P_{aw} = R_0 \dot{V} + R_1 \dot{V}^2 \quad (15)$$

With two samples in an inspiratory phase, the pressure-flow relation can be obtained by solving the following two equations:

$$\left.\frac{\Delta P_{aw}}{\Delta \dot{V}}\right|_{FSO1} = \left.(R_0 + 2R_1 \dot{V} \Delta \dot{V})\right|_{FSO1} \quad (16)$$

$$\left.\frac{\Delta P_{aw}}{\Delta \dot{V}}\right|_{FSO2} = \left.(R_0 + 2R_1 \dot{V} \Delta \dot{V})\right|_{FSO2} \quad (17)$$

Equations (16) and (17) represent the effects of two FSO's, called FSO1 and FSO2, provided at different times and different flow levels. $R_0$ and $R_1$ are derived from the above two equations, which are thus considered to be two simultaneous equations in two variables.

The FSO's frequency, amplitude, shape and timing are adjustable as functions of the S/N ratio, patient comfort and ventilator triggering. In a preferred embodiment of the present invention, one sinusoidal pressure oscillation having a frequency of 4 Hz and a pressure of 3 cm $H_2O$ is superimposed on the pressure delivered to the patient. It is to be understood, however, that other frequencies and pressures, such as a frequency in a range of 3–10 Hz and a pressure in the range of 2–10 cm $H_2O$ can be superimposed on the pressure delivered to the patient. Although, the frequency of the FSO is usually between 4 Hz and 15 Hz, the maximum frequency is limited by the bandwidth of the pressure controller. In short, the FSO technique provides an automatic, noninvasive and on-line method for evaluating respiratory resistance of a ventilator-supported patient. It can be implemented on existing ventilators as an add-on module or can used alone with a data processing module to facilitate flow-pressure peak identification and statistical analysis.

The second technique of the present invention is referred to as the pneumatic occlusion method, or POM, and it is used to determine the respiratory system's elastance $E_{rs}$. The POM works by blocking the patient's expiration momentary when an exhalation just starts. Unlike conventional techniques that block the patient's expiration mechanically using mechanical shutters or valves or by stopping the piston or bellows, the POM of the present invention pneumatically blocks the patient's airway by applying a pressure at the airway opening at the end of inspiration and at the onset of exhalation. The controlled pressure that provides the pneumatic occlusion is generated by the ventilator. Such pressure exerts a force on the airway opening having the same physical effects as mechanically blocking the air passage using conventional techniques.

Figure 5:
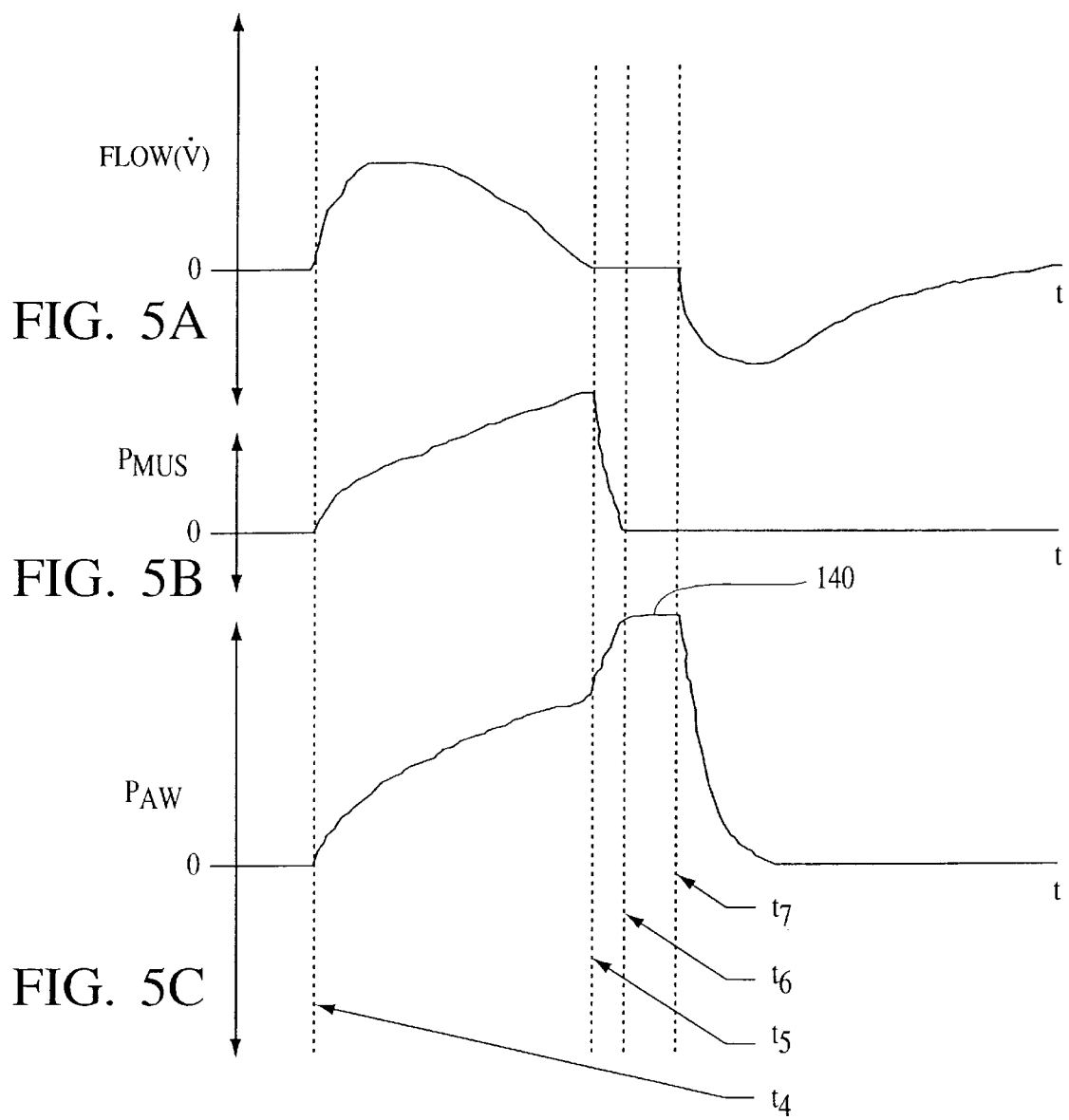
FIGS. 5A–5C illustrate a cycle of patient flow, effort, and pressure, respectively, describing the operation of the pressure occlusion method according to the principles of the present invention.

FIGS. 5A–5C illustrate a complete cycle of flow, patient effort and pressure at the airway opening during a normal PAV support interval ($t_4$–$t_5$) and during an occlusion ($t_5$–$t_7$). At time $t_4$, inspiration starts. At time $t_5$, expiration and occlusion start. In the interval between $t_5$ and $t_7$, the ventilator controls the pressure at the patient to make the patient's flow $\dot{V}$ substantially zero. During the interval from $t_5$ to $t_6$, the patient's muscle tone tapers off and reaches a relaxed state at time $t_6$. The duration of this interval is patient dependent and usually is under 250 ms. At time $t_6$, the patient's muscles are totally relaxed. When the equilibrium state is reached, the pressure at the airway opening and the elastic recoil pressure are balanced and a pressure plateau 140 is observed. At time $t_7$, the occlusion is removed, and the airway pressure is typically maintained at EPAP during the rest of the exhalation. Typically, the duration of time interval $t_5$–$t_7$ is approximately 400 ms. The elastic recoil pressure is a function of the patient's respiratory system volume and elastic property. Because the tidal volume is known, the pressure-volume relation or $E_{rs}$ can be obtained during the pressure equilibration.

Figure 6:
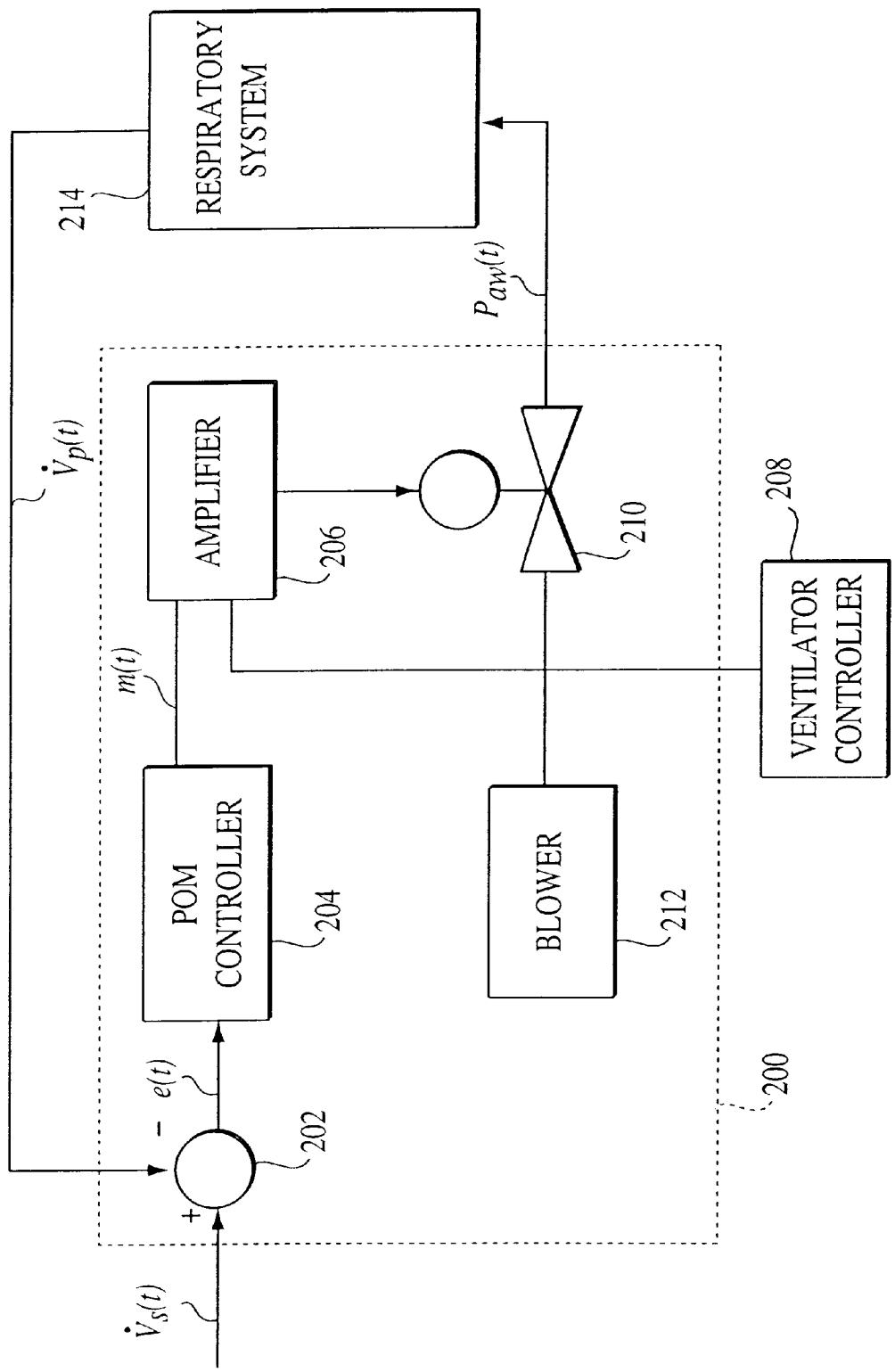
FIG. 6. is a schematic diagram of a ventilatory control system according to the principles of the present invention.

FIG. 6 is a schematic diagram of an exemplary embodiment of a POM control system 200 according to the principles of the present invention. In POM system 200, flow setting device 202 receives an operator input set flow signal $\dot{V}_s(t)$ to set the flow and an input of the measured patient flow $\dot{V}_p(t)$. Flow setting device 202 outputs a flow control error signal e(t) to POM controller (flow controller) 204. POM controller 204 and ventilator controller 208 provide control signals to amplifier 206, which controls valve 210 to vary the pressure supplied by blower 212 to the patient's respiratory system 214.

From a control point of view, system 200 shown can be thought of as a flow control system. The item being controlled is the human respiratory system, the variable being controlled is the flow to the respiratory system, and the system output is the pressure. The POM controller overrides the regular ventilator pressure controlling during the occlusion.

An important feature of POM is its POM controller. In the development of the controller, factors such as respiratory muscle movement characteristics, the ventilator's dynamic response and the ventilator's triggering sensitivity were all taken into consideration. POM does not require any special patient cooperation other than normal procedures required for ventilator support. The occlusion is quick enough so that the patient's reaction, if there is any, will not affect the results.

The operation of POM will now be explained with reference to a specific implementation thereof known as zero flow pressure control (ZFPC). Zero flow pressure control involves applying a pressure for a brief period of time (0.3–0.7 sec, for example) at the airway opening to occlude expiratory flow. The pressure application is activated at the very beginning of an expiration, when airway flow changes direction from entering the lung to exiting the lung. If the flow is maintained at zero, the applied pressure reaches its plateau, which equals elastic recoil force $P_{elastic}(t)$, but has the opposite direction. Because the flow is approximately zero, the patient's volume should remain approximately equal to the inspiratory tidal volume plus the functional residual capacity of the respiratory system.

The patient's effort (muscle pressure $P_{mus}$) does not change to zero suddenly when an expiration begins. Instead, there is a transition period, from $t_5$ to $t_6$. Thus, applied pressure presents a similar transition from its current level (e.g., IPAP) to its plateau level. When the equilibratory state is reached, the plateau pressure and the elastic pressure are equalized so that:

$$P_{plateau} = -P_{elastic}|_{\dot{V}(t)=0} \quad (18)$$

$E_{rs}$ can then be obtained by the following equation:

$$E_{rs} = \frac{P_{plateau} - EPAP}{V_{tidal}}, \quad (19)$$

where EPAP is the value of airway pressure $P_{aw}$ at the end of the expiration when the lung volume has the FRC value and where tidal volume $V_{tidal}$ is obtained by integrating the inspiratory flow over time.

As noted above with reference to FIG. 6, the POM of the present invention can be considered to be a flow control system. In this figure, m(t) is the controller's output to the valve which manipulates pressure $P_{aw}(t)$ delivered to the patient, $\dot{V}_s(t)$ is the flow set point, or the command signal, $\dot{V}_p(t)$ is the patient's flow and the feedback to the control system, and error e(t) is the difference between the patient's flow and the set flow so that:

$$e(t) = \dot{V}_s(t) - \dot{V}_p(t) \tag{20}$$

In the case of zero flow control, $\dot{V}_s(t)=0$, so that $$e(t) = -\dot{V}_p(t). \tag{21}$$

A proportional integral derivative (PID) control technique is applied in the controller. The general analog form of the PID control equation is expressed as:

$$m(t) = K_p e(t) + K_d \frac{d}{dt} e(t) + K_i \int e(t) dt \tag{22}$$

The discrete time equivalent of this equation is expressed as:

$$m(i) = K_p e(i) + \frac{K_d}{T}(e(ii) - e(i-1)) + TK_i \sum_{k=0}^{i} e(k) \tag{23}$$

where T is the sampling interval.

Because the control begins when the flow is approximately zero, it is more effective to control the relative change of the valve position according to the previous position. In an alternative algorithm, the PID velocity algorithm controls the relative change of the valve position so that:

$$\Delta m(i) = k_1 e(i) + k_2 e(i-1) + k_3 e(i-2) \tag{24}$$

where $$k_1 = K_p + TK_i + \frac{K_d}{T} \tag{25}$$

and $$k_2 = -\left(K_p + 2\frac{K_d}{T}\right) \tag{26}$$

and $$k_3 = \frac{K_d}{T} \tag{27}$$

The quantity $\Delta m(i)$ is added to the previous control output at each sample interval:

$$m(i) = m(i-1) + \Delta m(i) \tag{28}$$

The criteria for the PID controller are its stability and its response time.

Figure 7:
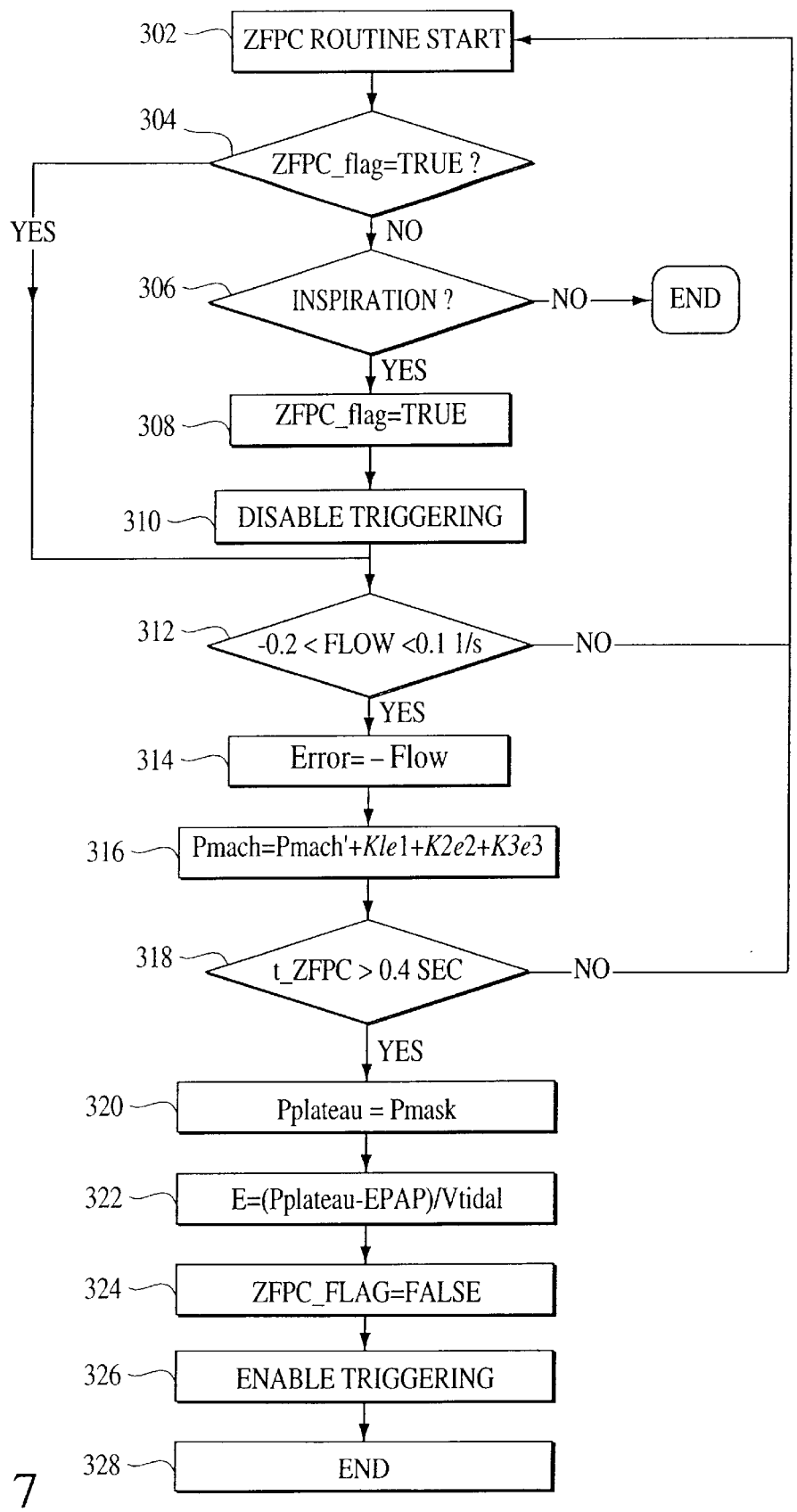
FIG. 7 is a flow chart illustrating the pressure occlusion method.

The flow chart of the ZFPC routine is shown in FIG. 7. Typically the routine POM is not performed during every patient breath. Instead, the POM is performed at a predetermined breathing frequency, such as every $5^{th}$, $10^{th}$, or $100^{th}$ breath. Alternatively, the POM can be performed based on the elapse of time, such as once every 5, 10 or 60 minutes, depending on the need to continuously update the PAV module or otherwise output the patient's current elastance.

The ZFPC routine, once initiated, starts in step 302 and advances to step 304, in which the routine determines whether flag ZFPC_Flag has its logical value set to TRUE (one), meaning that the zero pressure flow control will take place at the end of the inspiratory phase. If the ZPFC_Flag is not true in step 304, the routine determines in step 306 whether the patient is currently in the inspiratory phase of the respiratory cycle. If so, flag ZFPC_Flag has its value set to TRUE in step 308, pressure support triggering is disabled in step 310 and the routine continues to step 312. If not, the routine ends. If it is determined in step 304 that the patient is ZFPC_Flag has its value set to TRUE, the routine also moves to step 312.

In step 312 the routine determines whether flow $\dot{V}$ (represented by a variable called "flow") has a value between -0.2 l/s and 0 l/s. If the flow falls within this range, error e (represented by a variable called "error") has its value set to $-\dot{V}$ in step 314, and in step 316, variable "Pmach" (representing control signal m) has its value incremented by the value determined in Equation (23). Pmach calculated in step 316 is the current value of the pressure output by the pressure generator, i.e., ventilator, and Pmach' is the prior value of the pressure. In essence, steps 314 and 316 cause the pressure support device to create the pneumatic occlusion. In step 318, it is determined whether time t_ZFPC is greater than 0.4 sec, meaning that the pneumatic occlusion has been implemented a sufficient amount of time to cause the patient's respiratory system to reach an equilibrium. In which case, variable Pplateau, representing the plateau pressure, is set in step 320 to the current pressure value at the mask, Pmask, representing the pressure detected at the respiratory system. In step 322, the elastance is derived, and in step 324, flag ZFPC_Flag is set to a logical value of FALSE (zero). In step 326, triggering is enabled and the routine ends at step 323. If the determination of any of steps 312 and 318 yields a negative answer, the routine repeats beginning at step 302.

The 0.4 sec time period specified in step 318 is selected to be long enough to allow the patient's respiratory system to reach an equilibrium following the application of the pneumatic occlusion. It can be appreciated, however, that this time period can be set to a value other than 0.4 sec so long as the time period selected provides the same function. Namely, the time interval must be long enough to allow the patient's respiratory system to reach an equilibrium but not so long that the patient's comfort is compromised or the patient responds to the application of the occlusion. The selection of this interval and a range of exemplary suitable values are discussed in greater detail below.

ZFPC is discontinued if a large patient reaction is detected. Also, a limited flow range is allowed for ZFPC, currently from -0.2 l/s to 0.1 l/s (inspiration flow being defined as positive). At the end of an inspiration, when the flow has fallen below 0.1 l/s, ZFPC is activated to keep the flow around zero. If the patient has a large reaction and uses force to exhale, the instant flow will usually go under -0.2 l/s. When this happens, ZFPC is deactivated, and no measurements are performed. It is to be understood, that the limits of -0.2 l/s to 0.1 l/s are exemplary, and that other values can be used for this range.

The steps illustrated in FIG. 7, once initiated, are performed rapidly based on the speed of the microprocessor carrying out the routine. For this reason, it is permissible to keep the ZFPC flag at FALSE (zero) and the triggering disable even though one of the conditions in steps 312 or 318 have not been satisfied. The routine continues to execute steps 302–312 or steps 302–318 until the conditions specified in steps 312 and 318 are satisfied, which will occur during that breath, and, thereafter, continues through steps 320–326 to enable the triggering and reset the ZFPC flag to FALSE. It can be appreciated that each time the routine illustrated in FIG. 7 is executed, the ZFPC flag is initially false and triggering is enabled, but the ZFPC flag is immediately set to TRUE and triggering disabled once inspiration is detected. Thereafter, should the questions presented in steps 312 or 318 result in a no, the routine ends and repeats to step 302. However, this time, the ZFPC flag is TRUE and triggering is already disabled, so step 304 bypasses to step 312, skipping steps 306–310.

After monitoring module 106 determines the patient's current elastance $E_{rs}(t)$ and resistance $R_{rs}(t)$ as discussed above, these values are supplied to adapter algorithms $E_{rs}$, $R_{rs}$ analysis module 104, which uses these measurements, as discussed below, to determine the elastance and resistance, $E_{pav}(t)$ and $R_{pav}(t)$ to provide to PAV module 102 for use in determining the proper pressure support to provide to the patient. The general function of analysis module 104 is to maintain the stability of the operation of the PAV module by preventing rapid transient changes in the current values of elastance and resistance, $E_{rs}(t)$ and $R_{rs}(t)$, determined by monitoring module 106 from causing the function of the PAV module to become unstable. Rather than provide the current values of elastance and resistance, $E_{rs}(t)$ and $R_{rs}(t)$, determined by monitoring module 106 directly to the PAV module, analysis module 104 factors out aberrant current elastance and resistance, $E_{rs}(t)$ and $R_{rs}(t)$, values.

Figure 8:
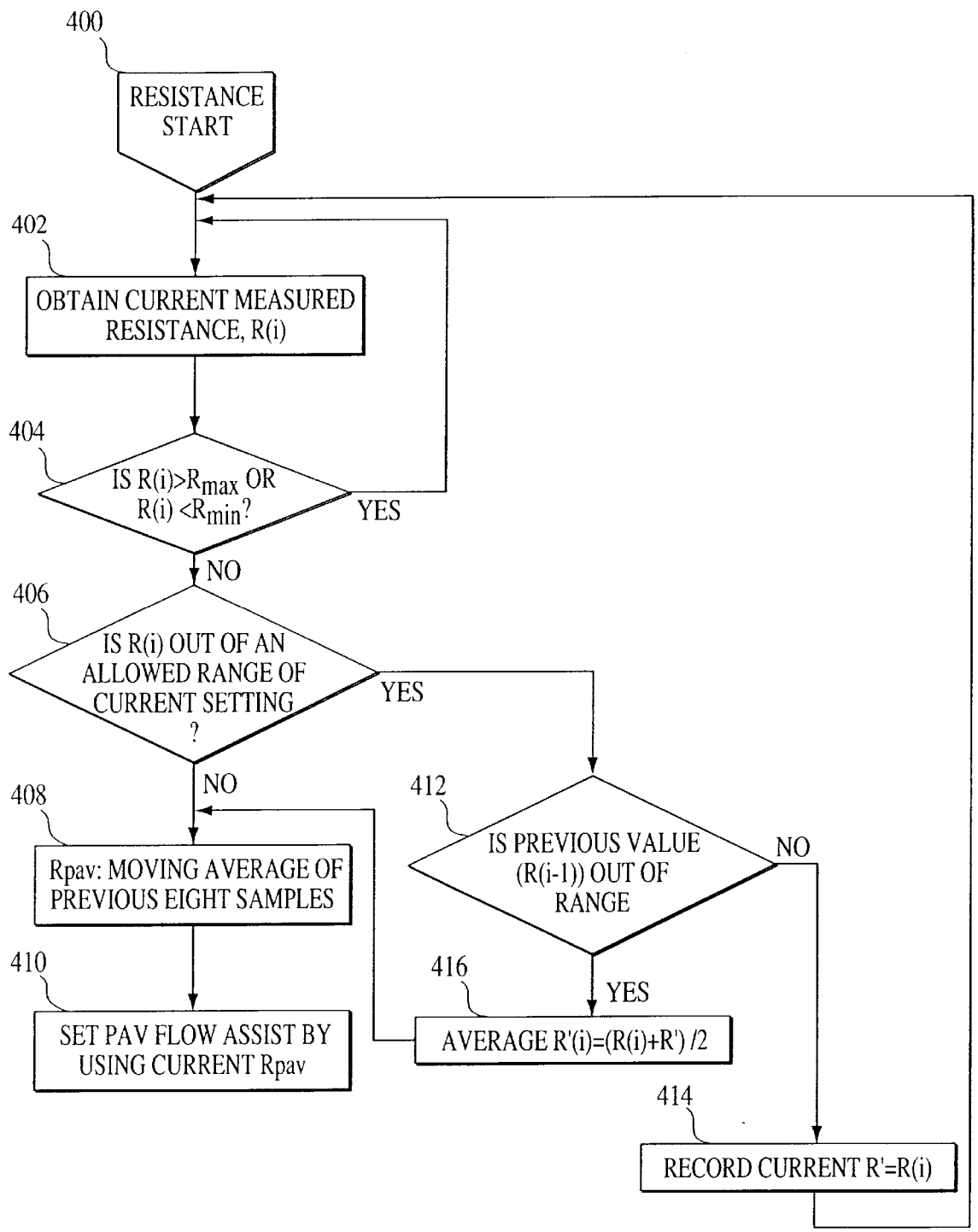
FIGS. 8 and 9 are flow charts illustrating the operation by which the resistance and elastance values used to control to respiratory assistance provided by the PAV module.
Figure 9:
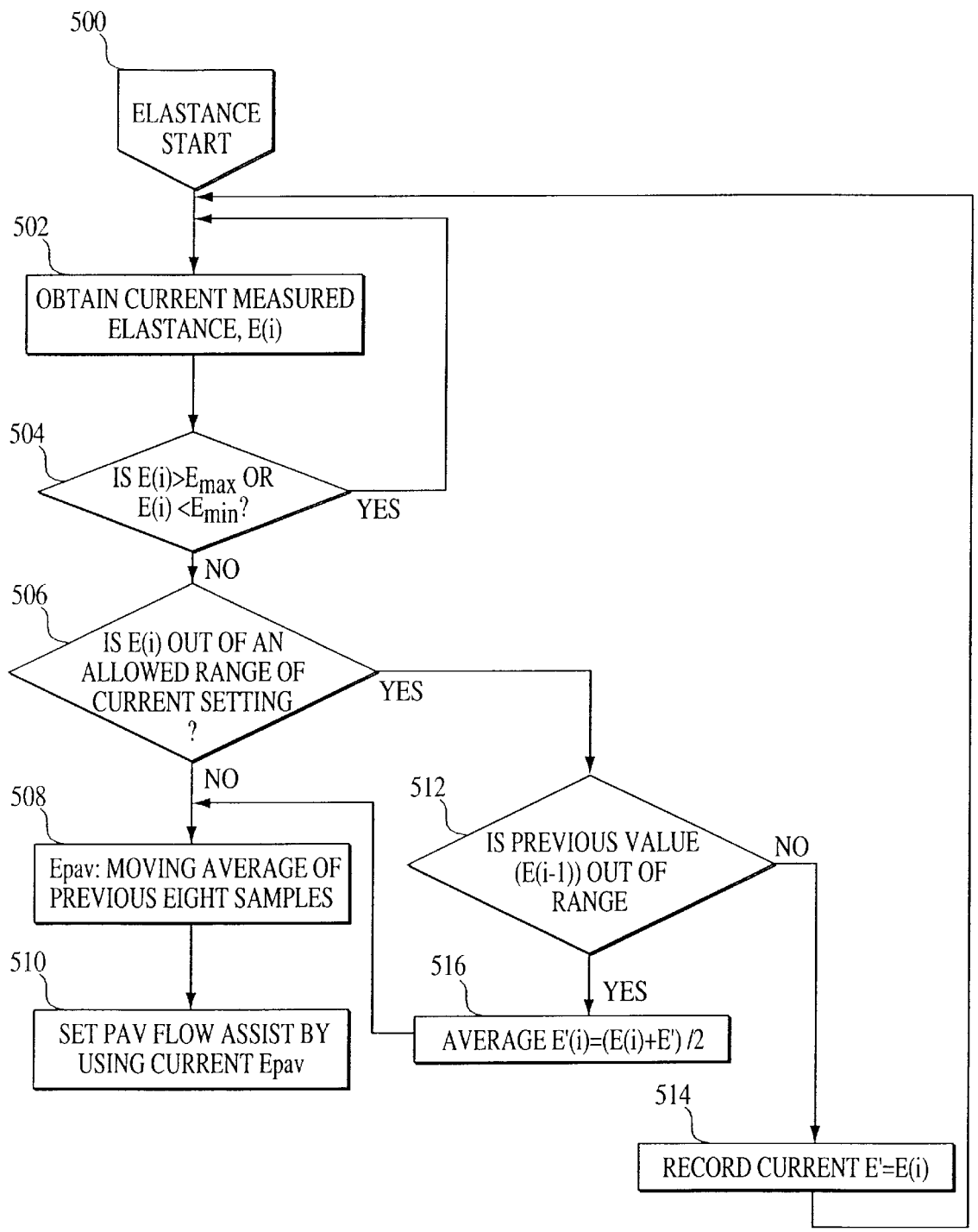

In a preferred embodiment of the present invention, adapter algorithms $E_{rs}$, $R_{rs}$ analysis module 104 determines the resistance and elastance, $R_{pav}(t)$ and $E_{pav}(t)$ to provide to PAV module 102 according to the routines illustrated in FIGS. 8 and 9, respectively. As shown in FIG. 8, the resistance value $R_{pav}(t)$ determination routine begins with step 400 and advances to step 402 where the current resistance value R(i) is obtained from monitoring module 106. The current resistance value R(i) corresponds, for example, to resistance value $R_{rs}$ determined using the routine illustrated in FIG. 4.

In step, 404 the routine determines if the current resistance value R(i) is greater than a maximum value Rmax or less than a minimum value Rmin. Any current resistance values outside the range from Rmax to Rmin are considered to be erroneous and are not used by the analysis module in determining the resistance $R_{pav}(t)$ to provide to PAV module 102. Exemplary values for Rmax and Rmin are 40 cm $H_2O$/liter/second and 1 cm $H_2O$/liter/second, respectively. Any current resistance value R(i) that is greater than 40 or less than 1 is rejected. If the current resistance is outside this range of acceptable values, the routine returns to step 402 and again determines the current resistance. Thus, step 404 serves as a filter to remove from consideration any resistance values outside maximum and minimum thresholds Rmax and Rmin. It is to be understood that the values for Rmax and Rmin can be selected taking into consideration the patient's disease state and the treatment being applied to the patient. Thus, the present invention is not intended to be limited to any specific values for Rmax and Rmin.

If the current resistance is within the acceptable physiologically possible range in step 404, the routine moves to step 406 where the routine compares the current resistance value to a second range of resistance values related to the current average of a predetermined number of resistance values preceding the current resistance value. This second range is a moving range that is based on the moving average value of a predetermined number of resistance values preceding the current resistance value, and, therefore, changes with the acceptable changes in the current resistance. If the patient's resistance rises, for example, the second range of resistance values related to the current average will also rise. In an exemplary embodiment of the present invention, the second range of resistance values is ±35% from the moving average of 8 resistance values preceding the current resistance value. It is to be understood, however, that the acceptable range and the number of resistance values selected to determined the average can be varied so long as the invention continues to function for its intended purpose.

If the current resistance value R(i) is not outside this second range associated with the average of a number of resistance values preceding the current resistance value, the routine moves to steps 408 and 410. In step 408 the routine determines the resistance $R_{pav}(t)$ to provide to PAV module 102 as the average of a predetermined number of previous resistance measurements. In step 410 resistance $R_{pav}(t)$ is used to control the flow provided by the PAV module 102. Thus, the routine recalculates the resistance value $R_{pav}(t)$ to provide to the PAV module if the current resistance R(i) is within the second range of resistance values.

If the current resistance value R(i) is outside this second range associated with the average of a number of resistance values preceding the current resistance value, the routine moves to step 412, and determines whether the previous resistance value R(i−1) is outside the second range. If not, the routine moves to step 414 and merely records the current resistance value, which then becomes the previous resistance value on the next pass through the routine of FIG. 8. If the previous resistance value is also outside the second range used in step 406, the routine moves to step 416 and averages the current resistance value R(i) and the previous resistance value R(i−1). This average R'(i) is used in step 408 to determine the resistance $R_{pav}(t)$ to provide to the PAV module.

In short, steps 406–416 compare the current resistance value to a range that is based on an average of a predetermined number of previously recorded resistance values. If the current resistance value is within this range, it is used to calculate a moving average that is then used to adjust the resistance provided to the PAV module. If, however, the current resistance value is outside the range used in step 406, the routine compares the previously recorded resistance value R(i−1) to the current range. If the previous resistance value is not outside the current range used in step 406, the routine records the current resistance value and does not alter the resistance value provided to the PAV module. If, however, the previous resistance value is outside the range in step 406, the previous resistance value and the current resistance value are averaged to this average is used to determine the resistance to provide to the PAV module. In effect, the first time the resistance value is outside the range based on a moving average in step 406 it is ignored for purposes of altering the resistance provided to the PAV module. If two consecutive resistance values are outside the range in step 406, the routine considers this to be a trend in the change of the patient's resistance and uses these resistance values to adjust the resistance provided to the PAV module, even though they are outside the range specified in step 406. It should be understood, however, that more than one previous resistance value can be used to determine when to alter the resistance provided to the PAV module.

The routine illustrated in FIG. 9 used to determine the elastance $E_{pav}(t)$ to provide to PAV module 102 is substantially the same as the routine illustrated in FIG. 8. Therefore, the routine illustrated in FIG. 9 will not be described in detail. It should be noted, however, that in an exemplary embodiment of the present invention, Emax and Emin used in step 504 are 90 cm $H_2O$/liter and 5 cm $H_2O$/liter, respectively.

Figure 10:
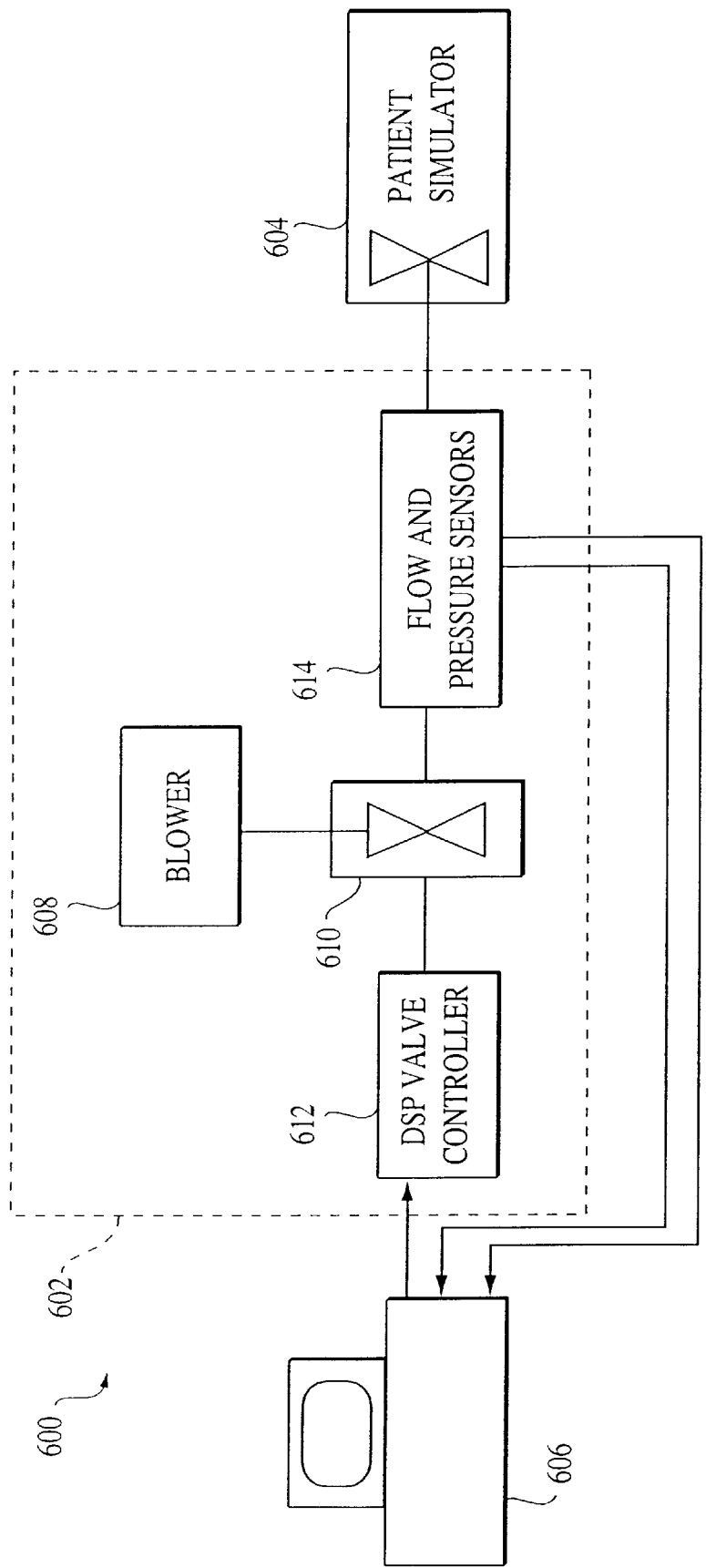
FIG. 10 is a schematic diagram of the APAV system of the present invention used on a simulated patient.

An experimental setup with a patient respiratory simulator was also used to test the present invention. The experimental setup is shown in FIG. 10. Experimental setup 600 includes the following three major parts: a pressure control 602 to provide PAV pressure support, a patient simulator 604 to simulate an active patient, and a processing system 606. Processing system 606 in the test, like that used to test FSO, includes a suitable processor, such as a Pentium Pro®.

In an exemplary embodiment of the present invention, pressure control system 602 includes a blower 608 with a maximum pressure of 20 cm H$_2$O, a sleeve valve 610, a DSP controller 612, such as the Texas Instruments TMS 320C26 DSP controller, and software running on the processor with spontaneous PAV/bilevel pressure support application algorithms. The pressure control system serves as a PAV/bilevel pressure support system with ZFPC capacity. Pressure and flow sensors 614 provide feedback of the pressure and flow provided to the patient to processing system 606. A controlled patient flow is achieved in this example by using an active lung patient simulator 604 rather than a patient. The active lung simulator models the spontaneously breathing of a patient and is responsive to pressure $P_{aw}$ at its airway opening.

In this configuration, processing system 606 generates the simulated patient, monitors the flow/pressure signals and processes the data. Pressure and flow sensors 614 measure the pressure and flow at the airway opening. In an exemplary embodiment, the data input and control output are achieved through an analog/digital I/O interface board. A valve control program is provided in the memory of DSP controller 612 via processor 606. A digital low-pass filter, e.g., 8 Hz, is used to limit the noise in the flow signal input.

The effects of unknown system leak on ZFPC will now be described. The patient flow is estimated according to the total flow from the ventilator (measurable) and the estimated leak. If there is a 10% error in the flow estimation and the ZFPC duration is 0.4 second, the air volume in the lungs at the end of ZFPC is no longer the same as the known tidal volume because actual patient flow is not exactly zero. If it is further assumed that the estimated flow is 10% larger than the actual patient flow, zero estimated patient flow means 0.1 l/s of actual expiration flow. The air volume lost during 0.4 second is approximately 0.04 l. Thus, the volume above FRC at the end of ZFPC is given by:

$$V_{ZFPC} = V_{tidal} - 0.04 \quad (29)$$

When the effect of resistance force at this low flow rate is ignored, $E_{rs}$ is obtained by the following equation:

$$E_{rs} = \frac{P_{plateau} - EPAP}{V_{ZFPC}} \quad (30)$$

Because $V_{tidal}$ is used instead of actual volume $V_{ZFPC}$ in the ZFPC mathematical operations, the calculated elastance is given by the following equation:

$$E'_{rs} = \frac{P_{plateau} - EPAP}{V_{tidal}} \quad (31)$$

The preceding two equations can be combined to give the relationship between true elastance $E_{rs}$ and calculated elastance $E'_{rs}$ obtained through ZFPC:

$$E'_{rs} = \frac{V_{ZFPC}}{V_{tidal}} E_{rs} \quad (32)$$

and $$E^1_{rs} = \left(1 - \frac{0.04}{V_{tidal}}\right) E_{rs} \quad (33)$$

When $V_{tidal}$ is assumed to be correct and has a value of 0.75 liter, the difference will be 5.3%.

The time the ZFPC is initiated is important to the accuracy and reliability of the measurement. If ZFPC is executed before an expiration starts, the subject's $P_{mus}$ is still active. On the other hand, if ZFPC is provided too late after the beginning of an expiration, a sudden reversal in flow will cause patient discomfort and may trigger a muscle reflex in the patient. The duration of ZFPC is preferably between 0.2 sec and 0.5 sec to allow the pressure to reach its plateau (equilibrating state). The current duration of the ZFPC routine is set around 0.4 msec, which is believed to cause no noticeable discomfort to the patient.

The POM technique discussed above can be implemented in any pressure or volume controlled ventilator without significant structure alteration. Such implementation requires no significant hardware changes for ventilators equipped with embedded microprocessors. Furthermore, no human operator is required. The procedure is activated according to the ventilator's internal triggering mechanism.

No methods are known that provide dynamic measurements of the patient's respiratory mechanics while allowing for leaks in the patient circuit. The POM technique of the present invention, however, applies pressure directly at the airway opening; therefore, leaks between the patient and the ventilator do not affect the occlusion. POM also works well with non-leak systems.

While two preferred embodiments of the present invention have been set forth, those skilled in the art who have reviewed this disclosure will readily appreciate that other embodiments can be derived within the scope of the invention. For example, the modifications to a standard ventilator can take the form of an add-on device which controls the ventilator, an upgrade to the ventilator's own internal software, or a combination of the two. Furthermore, the present invention can be implemented using a variety of processors and a variety of ventilators. The modifications set forth in this disclosure can be combined as needed. APAV can be implemented with one or both of FSO and POM or with other techniques for measuring $E_{rs}$, or $R_{rs}$.

Although the invention has been described in detail for the purpose of illustration based on what is currently considered to be the most practical and preferred embodiments, it is to be understood that such detail is solely for that purpose and that the invention is not limited to the disclosed embodiments, but on the contrary, is intended to cover modifications and equivalent arrangements that are within the spirit and scope of the appended claims.

What is claimed is:

1. A ventilator system comprising:
   (a) ventilation means for delivering a therapeutic pressure to the respiratory system of a patient;
   (b) respiratory mechanics monitoring means for detecting a resistance of the respiratory system of the patient and for outputting the detected resistance, wherein the respiratory mechanics monitoring means comprises:
      (i) forced single oscillation means, in communication with the ventilation means, for controlling the ventilation means to superimpose at least one single pressure oscillation upon the therapeutic pressure during an inspiratory phase of the therapeutic pressure to obtain a forced single oscillation superimposed therapeutic pressure that is delivered to the patient, the single pressure oscillation having a maximum at time $t_1$ and a minimum at time $t_2$, and (ii) patient response monitoring means for monitoring a response by the patient to the forced single oscillation superimposed on the therapeutic pressure to determine the resistance in accordance with the response; and (c) adapter means, receiving the detected resistance output by the respiratory mechanics monitoring means, for controlling the ventilation means to adjust the therapeutic pressure in accordance with the detected resistance.

2. A ventilator system as in claim 1, wherein the forced single oscillation means superimposes two single pressure oscillations upon the therapeutic pressure during a single inspiratory phase of the therapeutic pressure, the two single pressure oscillations being separated by a non-zero time interval, and wherein the times at which the patient response monitoring means monitors the responses to determine the resistance include times associated with the two separated single pressure oscillations.

3. A ventilator system as in claim 1, wherein at any time t during which the patient response monitoring means operates, the patient response monitoring means detects an airway pressure $P_{aw}(t)$ and a respiratory system flow $\dot{V}(t)$; and wherein the resistance $R_{rs}$ is given by:

$$R_{rs} = \frac{P_{aw}(t_1) - P_{aw}(t_2)}{\dot{V}(t_1) - \dot{V}(t_2)}.$$

4. A ventilator system as in claim 1, wherein
the single pressure oscillation has a beginning time $t_0$ and an end time $t_3$;
at any time t during which the patient response monitoring means operates, the patient response monitoring means detects an airway pressure $P_{aw}(t)$ and a respiratory system flow $\dot{V}(t)$;
an offset flow $\dot{V}_{offset}(t)$ is defined as $\dot{V}_{offset}(t) = \dot{V}(t_0) - \dot{V}(t_3)$; and
the resistance $R_{rs}$ is given by:

$$R_{rs} = \frac{P_{aw}(t_1) - P_{aw}(t_2)}{\dot{V}(t_1) - \dot{V}(t_2) - \frac{\dot{V}_{offset}}{2}}.$$

5. A ventilator system comprising:
(a) ventilation means for delivering a therapeutic pressure to the respiratory system of a patient;
(b) respiratory mechanics monitoring means for detecting an elastance of the respiratory system of the patient and for outputting the detected elastance, wherein the respiratory mechanics monitoring means comprises:
(i) a pneumatic occlusion means, in communication with the ventilation means, for controlling the ventilation means to superimpose at least one occluding pressure upon the therapeutic pressure during an occluding time period within an expiratory phase of the therapeutic pressure to obtain a temporarily occluded therapeutic pressure that is delivered to the patient, the occluding pressure being such that during the occluding time period, patient air flow is substantially zero, and (ii) patient response monitoring means for monitoring a response by the patient to the temporarily occluded therapeutic pressure at a time associated with the occluding time period to determine the elastance; and (c) adapter means, receiving the detected elastance output by the respiratory mechanics monitoring means, for controlling the ventilation means to adjust the therapeutic pressure in accordance with the detected elastance.

6. A ventilator system as in claim 5, wherein a beginning of the occluding time period coincides with a beginning of the expiratory phase.

7. A ventilator system as in claim 5, wherein:
at an end of the expiratory phase, the therapeutic pressure has a value EPAP;
at an end of the occluding time period, the respiratory system is subjected to plateau pressure $P_{plateau}$;
during an inspiratory phase, the respiratory system increases in volume by $V_{tidal}$; and
the elastance is given by:

$$E_{rs} = \frac{P_{plateau} - EPAP}{V_{tidal}}.$$

8. A ventilator system as in claim 5, wherein:
the patient response monitoring means comprises means for detecting flow $\dot{V}_p(t)$ of the respiratory system; and
the adapter means comprises means for (i) receiving an input of set flow $\dot{V}_s(t)$, (ii) deriving error $e(t)$ such that $e(t) = \dot{V}_s(t) - \dot{V}_p(t)$, (iii) deriving control signal $m(t)$ in accordance with $e(t)$, a time derivative of $e(t)$ and a time integral of $e(t)$ and (iv) controlling the ventilation means to adjust the therapeutic pressure in accordance with $m(t)$.

9. A ventilator system as in claim 5, wherein the patient response monitoring means comprises:
means for detecting flow in the respiratory system and determining whether the flow in the respiratory system falls within a predetermined range; and
means for stopping operation of the occlusion means when the flow in the respiratory system does not fall within the predetermined range.

10. A ventilator system comprising:
(a) ventilation means for delivering a therapeutic pressure to the respiratory system of a patient;
(b) respiratory mechanics monitoring means for detecting at least one of a resistance and an elastance of the respiratory system of the patient and for outputting the detected resistance and elastance, wherein the respiratory mechanics monitoring means comprises:
(i) forced single oscillation means, in communication with the ventilation means, for controlling the ventilation means to superimpose at least one single pressure oscillation upon the therapeutic pressure during an inspiratory phase of the therapeutic pressure to obtain a forced single oscillation superimposed therapeutic pressure which is delivered to the patient, the at least one single pressure oscillation having a maximum at time $t_1$ and a minimum at time $t_2$,
(ii) first patient response monitoring means for monitoring a response by the patient to the forced single oscillation superimposed therapeutic pressure to determine the resistance in accordance with the response, (iii) occlusion means, in communication with the ventilation means, for controlling the ventilation means to superimpose at least one occluding pressure upon the therapeutic pressure during an occluding time period within an expiratory phase of the therapeutic pressure to obtain a temporarily occluded therapeutic pressure which is delivered to the patient, the occluding pressure being such that during the occluding time period, patient air flow is substantially zero, and (iv) second patient response monitoring means for monitoring a response by the patient to the temporarily occluded therapeutic pressure during the occluding time period to determine the elastance; and (c) adapter means, receiving the detected resistance and elastance output by the respiratory mechanics monitoring means, for controlling the ventilation means to adjust the therapeutic pressure in accordance with the detected resistance and elastance.

11. A method for adaptively assisting a function of a respiratory system of a patient, the method comprising:

(a) controlling a ventilator to deliver a therapeutic pressure to the respiratory system of the patient;

(b) controlling the ventilator to superimpose at least one single pressure oscillation upon the therapeutic pressure during an inspiratory phase of the therapeutic pressure to obtain a forced single oscillation superimposed therapeutic pressure which is delivered to the patient, the at least one single pressure oscillation having a maximum at time $t_1$ and a minimum at time $t_2$;

(c) monitoring a response by the patient to the forced single oscillation superimposed therapeutic pressure to determine a resistance of the respiratory system of the patient in accordance with the response; and (d) controlling the ventilator to adjust the therapeutic pressure in accordance with the resistance determined in step (c).

12. A method as in claim 11, wherein step (b) comprises superimposing two single pressure oscillations upon the therapeutic pressure during a single inspiratory phase of the therapeutic pressure, the two single pressure oscillations being separated by a non-zero time interval, and the times at which the responses are monitored to determine the resistance and the elastance comprise times associated with both of the two separated single pressure oscillations.

13. A method as in claim 11, wherein:

at any time t during which the response is monitored, an airway pressure $P_{aw}(t)$ and a respiratory system flow $\dot{V}(t)$ are detected; and the resistance $R_{rs}$ is given by:

$$R_{rs} = \frac{P_{aw}(t_1) - P_{aw}(t_2)}{\dot{V}(t_1) - \dot{V}(t_2)}.$$

14. A method as in claim 11, wherein:

the at least one single pressure oscillation has a beginning time $t_0$ and an end time $t_3$;

at any time t during which responses are monitored, an airway pressure $P_{aw}(t)$ and a respiratory system flow $\dot{V}(t)$ are detected;

an offset flow $\dot{V}_{offset}(t)$ is defined as $\dot{V}_{offset}(t)=\dot{V}(t_0)-\dot{V}(t_3)$; and the resistance $R_{rs}$ is given by:

$$R_{rs} = \frac{P_{aw}(t_1) - P_{aw}(t_2)}{\dot{V}(t_1) - \dot{V}(t_2) - \dfrac{\dot{V}_{offset}}{2}}.$$

15. A method for adaptively assisting a function of a respiratory system of a patient, the method comprising:

(a) controlling a ventilator to deliver a therapeutic pressure to the respiratory system of the patient;

(b) controlling the ventilator to superimpose at least one occluding pressure upon the therapeutic pressure during an occluding time period within an expiratory phase of the therapeutic pressure to obtain a temporarily occluded therapeutic pressure which is delivered to the patient, the occluding pressure being such that during the occluding time period, patient air flow is substantially zero; and (c) monitoring a response by the patient to the temporarily occluded therapeutic pressure during the occluding time period to determine an elastance of the respiratory system of the patient; and (d) controlling the ventilator to adjust the therapeutic pressure in accordance with the elastance determined in step (c).

16. A method as in claim 15, wherein a beginning of the occluding time period coincides with a beginning of the expiratory phase.

17. A method as in claim 15, wherein:

at an end of the expiratory phase, the therapeutic pressure has a value EPAP;

at an end of the occluding time period, the respiratory system is subjected to plateau pressure $P_{plateau}$;

during an inspiratory phase, the respiratory system increases in volume by $V_{tidal}$; and the elastance is given by:

$$E_{rs} = \frac{P_{plateau} - EPAP}{V_{tidal}}.$$

18. A method as in claim 15, wherein:

flow $\dot{V}_p(t)$ of the respiratory system is detected; and step (c) comprises (i) receiving an input of set flow $\dot{V}_s(t)$, (ii) deriving error e(t) such that $e(t)=\dot{V}_s(t)-\dot{V}_p(t)$, (iii) deriving control signal m(t) in accordance with e(t), a time derivative of e(t) and a time integral of e(t) and (iv) controlling the ventilator to adjust the therapeutic pressure in accordance with m(t).

19. A method as in claim 15, wherein step (c) comprises:

detecting flow in the respiratory system and determining whether the flow in the respiratory system falls within a predetermined range; and stopping step (b) when the flow in the respiratory system does not fall within the predetermined range.

20. A method for adaptively assisting a function of a respiratory system of a patient, the method comprising:

(a) controlling a ventilator to deliver a therapeutic pressure to the respiratory system of the patient;

(b) controlling the ventilator to superimpose at least one single pressure oscillation upon the therapeutic pressure during an inspiratory phase of the therapeutic pressure to obtain a forced single oscillation superimposed therapeutic pressure which is delivered to the patient, the at least one single pressure oscillation having a maximum at time $t_1$ and a minimum at time $t_2$;

(c) monitoring a response by the patient to the forced single oscillation superimposed therapeutic pressure to determine a resistance of a respiratory system of the patient in accordance with the response;

(d) controlling the ventilator to superimpose at least one occluding pressure upon the therapeutic pressure during an occluding time period within an expiratory phase of the therapeutic pressure to obtain a temporarily occluded therapeutic pressure which is delivered to the patient, the occluding pressure being such that during the occluding time period, patient air flow is substantially zero; and (e) monitoring a response by the patient to the temporarily occluded therapeutic pressure during the occluding time period to determine an elastance of a respiratory system of the patient; and (f) controlling the ventilator to adjust the therapeutic pressure in accordance with the resistance determined in step (c) and the elastance determined in step (e).

21. A system for detecting a resistance of a respiratory system of a patient, the detecting system comprising:

forced single oscillation means, in communication with a ventilation means for delivering a therapeutic pressure to the patient, for controlling the ventilation means to superimpose at least one single pressure oscillation upon the therapeutic pressure during an inspiratory phase of the therapeutic pressure to obtain a forced single oscillation superimposed therapeutic pressure which is delivered to the patient, the at least one single pressure oscillation having a maximum at time $t_1$ and a minimum at time $t_2$; and patient response monitoring means for monitoring a response by the patient to the forced single oscillation superimposed therapeutic pressure to determine the resistance in accordance with the response.

22. A system as in claim 21, wherein:

the forced single oscillation means superimposes two single pressure oscillations upon the therapeutic pressure during a single inspiratory phase of the therapeutic pressure, the two single pressure oscillations being separated by a non-zero time interval; and the times at which the patient response monitoring means monitors the responses to determine the resistance and the elastance comprise times during both of the two separated single pressure oscillations.

23. A system as in claim 21, wherein:

at any time t during which the patient response monitoring means operates, the patient response monitoring means detects an airway pressure $P_{aw}(t)$ and a respiratory flow $\dot{V}(t)$; and the resistance $R_{rs}$ is given by:

$$R_{rs} = \frac{P_{aw}(t_1) - P_{aw}(t_2)}{\dot{V}(t_1) - \dot{V}(t_2)}.$$

24. A system as in claim 21, wherein:

the at least one single pressure oscillation has a beginning time $t_0$ and an end time $t_3$;

at any time t during which the patient response monitoring means operates, the patient response monitoring means detects an airway pressure $P_{aw}(t)$ and a respiratory system flow $\dot{V}(t)$;

an offset flow $\dot{V}_{offset}(t)$ is defined as $\dot{V}_{offset}(t) = \dot{V}(t_0) - \dot{V}(t_3)$; and the resistance $R_{rs}$ is given by:

$$R_{rs} = \frac{P_{aw}(t_1) - P_{aw}(t_2)}{\dot{V}(t_1) - \dot{V}(t_2) - \frac{\dot{V}_{offset}}{2}}.$$

25. A system for detecting an elastance of a respiratory system of a patient, the detecting system comprising:

occlusion means, in communication with ventilation means for delivering a therapeutic pressure to a patient, for controlling the ventilation means to superimpose at least one occluding pressure upon the therapeutic pressure during an occluding time period within an expiratory phase of the therapeutic pressure to obtain a temporarily occluded therapeutic pressure which is delivered to the patient, the occluding pressure being such that during the occluding time period, patient air flow is substantially zero; and patient response monitoring means for monitoring a response by the patient to the temporarily occluded therapeutic pressure during the occluding time period to determine the elastance.

26. A system as in claim 25, wherein a beginning of the occluding time period coincides with a beginning of the expiratory phase.

27. A system as in claim 25, wherein:

at an end of the expiratory phase, the therapeutic pressure has a value EPAP;

at an end of the occluding time period, the respiratory system is subjected to plateau pressure $P_{plateau}$;

during an inspiratory phase, the respiratory system increases in volume by $V_{tidal}$; and the elastance is given by:

$$E_{rs} = \frac{P_{plateau} - EPAP}{V_{tidal}}.$$

28. A method for detecting a resistance of a respiratory system of a patient, the method comprising:

(a) controlling a ventilator to deliver a therapeutic pressure to the respiratory system of the patient;

(b) controlling a ventilator to superimpose at least one single pressure oscillation upon the therapeutic pressure during an inspiratory phase of the therapeutic pressure to obtain a forced single oscillation superimposed therapeutic pressure which is delivered to the patient, the at least one single pressure oscillation having a maximum at time $t_1$ and a minimum at time $t_2$; and (c) monitoring a response by the patient to the forced single oscillation superimposed therapeutic pressure to determine a resistance in accordance with the response.

29. A method as in claim 28, wherein step (b) comprises superimposing two single pressure oscillations upon the therapeutic pressure during a single inspiratory phase of the therapeutic pressure, the two single pressure oscillations being separated by a non-zero time interval and the times at which the response is monitored to determine the resistance comprise times during both of the two separated single pressure oscillations.

30. A method as in claim 28, wherein:

at any time t during which the response is monitored, an airway pressure $P_{aw}(t)$ and a respiratory system flow $\dot{V}(t)$ are detected; and the resistance $R_{rs}$ is given by:

$$R_{rs} = \frac{P_{aw}(t_1) - P_{aw}(t_2)}{\dot{V}(t_1) - \dot{V}(t_2)}.$$

31. A method as in claim 28, wherein:

the at least one single pressure oscillation has a beginning time $t_0$ and an end time $t_3$;

at any time t during which responses are monitored, an airway pressure $P_{aw}(t)$ and a respiratory flow $\dot{V}(t)$ are detected;

an offset flow $\dot{V}(t)$ is defined as $\dot{V}_{offset}(t) = \dot{V}(t_0) - \dot{V}(t_3)$; and the resistance $R_{rs}$ is given by:

$$R_{rs} = \frac{P_{aw}(t_1) - P_{aw}(t_2)}{\dot{V}(t_1) - \dot{V}(t_2) - \frac{\dot{V}_{offset}}{2}}.$$

32. A method for detecting an elastance of a respiratory system of a patient, the method comprising:

(a) controlling a ventilator to deliver a therapeutic pressure to the respiratory system of the patient;

(b) controlling the ventilator to superimpose at least one occluding pressure upon the therapeutic pressure during an occluding time period within an expiratory phase of the therapeutic pressure to obtain a temporarily occluded therapeutic pressure which is delivered to the patient, the occluding pressure being such that during the occluding time period, patient air flow is substantially zero; and (c) monitoring responses by the patient to the temporarily occluded therapeutic pressure during the occluding time period to determine the elastance.

33. A method as in claim 32, wherein a beginning of the occluding time period coincides with a beginning of the expiratory phase.

\* \* \* \* \*